US007851658B2

(12) United States Patent
Liu et al.

(10) Patent No.: US 7,851,658 B2
(45) Date of Patent: Dec. 14, 2010

(54) PALLADIUM-CATALYZED CARBON-CARBON BOND FORMING REACTIONS

(75) Inventors: David R. Liu, Lexington, MA (US); Matthew W. Kanan, Cambridge, MA (US); Mary M. Rozenman, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 337 days.

(21) Appl. No.: 11/205,493

(22) Filed: Aug. 17, 2005

(65) Prior Publication Data

US 2007/0066851 A1 Mar. 22, 2007

Related U.S. Application Data

(60) Provisional application No. 60/602,255, filed on Aug. 17, 2004.

(51) Int. Cl.
C07C 45/00 (2006.01)
(52) U.S. Cl. .................. 568/395; 540/454; 564/169
(58) Field of Classification Search ................ 540/454; 564/169; 568/395
See application file for complete search history.

(56) References Cited

U.S. PATENT DOCUMENTS

| | | | |
|---|---|---|---|
| 4,835,312 | A | 5/1989 | Itoh et al. |
| 5,457,111 | A | 10/1995 | Luly et al. |
| 5,677,467 | A | 10/1997 | Hoye et al. |
| 5,880,280 | A | 3/1999 | Organ et al. |
| 6,368,808 | B2 | 4/2002 | Sato et al. |
| 6,387,901 | B1 | 5/2002 | Chupak |
| 6,700,025 | B2 | 3/2004 | Moriarty et al. |
| 6,774,229 | B2 | 8/2004 | Mueller et al. |
| 2004/0018042 | A1 | 1/2004 | Smith et al. |

OTHER PUBLICATIONS

Chiusoli et al, Gazzetta Chimica Italiana, 1987, 117(1), 695-700.*
Breslow, et al., "Biomimetric Chemistry and Artificial Enzymes: Catalysis by Design." *Acc. Chem. Res.* 28: 146-153, 1995.
Burrows, et al., "Oxidative Nucleobase Modifications Leading to Strand Scisson" *Chem. Rev.* 98: 1109-1152, 1998.
Calderone, et al., "Directing Otherwise Incompatible Reactions in a Single Solution by Using DNA-Templated Organic Synthesis." *Angew. Chem. Int. Ed.* 41: 4104-8, 2002.
Corey, et al., *J. Org. Chem.* 51: 1925-1926, 1986.
Cotarca, et al., *Synthesis* 328-332, 1997.
Delia, et al., *Heterocycles* 35: 1397-1410, 1993.
Evans, et al., "Proton-Activated Fluorescence As a Tool for Simultaneous Screening of Combinatorial Chemical Reactions." *Curr. Opin. Chem. Biol.* 6: 333-338, 2002.
Gartner, et al., "The Generality of DNA-Templated Synthesis As a Basis for Evolving Non-Natural Small Molecules" *J. Am. Chem. Soc.* 123: 6961-3, 2001.

Gartner, et al., "Expanding the Reaction Scope of DNA-Templated Synthesis." *Angew Chem. Int. Ed.* 41: 1796-1800, 2002.
Heck, et al., "Palladium-Catalyzed Vinylation of Organic Halides" *Org. React.* 27: 345, 1982.
Joyce, et al., "Directed Evolution of Nucleic Acid Enzymes" *Annu. Rev. Biochem.* 73: 791-836, 2004.
Kohli, et al., Biomimetric Synthesis and Optimization of Cyclic Peptide Antibiotics. *Nature* 418: 658-61, 2002.
Kusumoto, et al., *Bull. Chem. Soc. Jpn.* 59: 1296-1298, 1986.
Li, et al., "Stereoselectivity in DNA-Templated Organic Synthesis and Its Origins." *J. Am. Chem. Soc.* 125: 10188-9, 2003.
Lober, et al., "Palladium-Catalyzed Hydroamination of 1,3-Dienes: A Coloimetric Assay and Enantioselective Additions." *J. Am. Chem. Soc.* 123: 4366-7, 2001.
Miyaura, et al., "Palladium-Catalyzed Cross-Coupling Reactions of Organoboron Compounds." *Chem. Rev.* 95: 2457-2483, 1995.
Oku, et al., *J. Org. Chem.* 65: 1899-1906, 200.
Reetz, et al., "Combinatorial and Evolution-Based Methods in the Creation of Anantioselective Catalysts" *Angew. Chem. Int. Ed.* 40: 284-310, 2001.
Rosenbaum, et al., "Efficient and Sequence-Specific DNA-Templated Polymerization of Peptide Nucleic Acid Aldehydes." *J. Am. Chem. Soc.* 125: 13924-5, 2003.
Rostovtsev, et al., "A Stepwise Huisgen Cycloaddition Process: Copper(I)-Catalyzed Regioselective 'Ligation' of Azides and Terminal Alkynes." *Angew. Chem. Int. Ed.* 41: 2596-9, 2002.
Schultz, et al.,. "Completing the Circle." *Nature* 418: 485, 2002.
Smidt, et al., *Angew. Chem.* 71: 176-182, 1959.
Smidt, et al., *Angew Chem* 74: 93-102, 1962.
Stambuli, et al., "Recent Advances in the Discovery of Organometallic Catalysts Using High-Throughput Screening Assays" *Curr. Opin. Chem. Biol.* 7: 420-426, 2003.
Stambuli, et al., "Screening of homogenous Catalysts by Fluorescence Resonance Energy Transfer. Identification of Catalysts for Room-Temperature Heck Reactions." *J. Am. Chem. Soc.* 123: 2677-8, 2001.
Staunton, et al., "Polyketide Biosynthesis: A Millennium Review." *Nat. Prod. Rep.* 18: 380-416, 2001.
Taylor, et al, "Thermographic Selection of Effective Catalysts From an Encoded Polymer-Bound Library." *Science* 280: 267-70, 1998.
Wadsworth, et al., "Utility of Phosphate Carbanions in Olefin Synthesis" *J. Am. Chem.* 83: 1733-8, 1961.

(Continued)

*Primary Examiner*—Shailendra Kumar
(74) *Attorney, Agent, or Firm*—Wolf, Greenfield & Sacks, P.C.; C. Hunter Baker

(57) ABSTRACT

A novel palladium-mediated carbon-carbon bond forming reaction has been discovered using DNA-templated chemistry. The inventive reaction involves the palladium-mediated coupling of a terminal alkyne with an alkene to form an enone. A catalytic amount of palladium may be used in the reaction if an oxidant is present. The reactions is also compatible with a variety of organic solvent as well as aqueous solution. Both intermolecular and intramolecular reactions have been demonstrated. This novel carbon-carbon bond forming reaction is particularly useful in the synthesis of macrocycles. Kits, reagents, catalysts, solvents, oxidants, salts, acids, instructions, and other materials useful in the practice of the inventive reaction are also provided.

5 Claims, 12 Drawing Sheets

OTHER PUBLICATIONS

Wang, et al., "Bioconjugation by Copper(I)-Catalyzed Azide-Alkyne [3+2] Cycloaddition." *J. Am. Chem. Soc.* 125: 3192-3, 2003.

Wilson, et al., "In Vitro Selection of Functional Nucleic Acids." *Annu. Rev. Biochem.* 68: 611-647, 1999.

International Search Report and Written Opinion for PCT/US2005/029294 mailed Aug. 2, 2007.

International Preliminary Report on Patentability for PCT/US2005/029294 mailed Sep. 7, 2007.

Kanan et al., Reaction discovery enabled by DNA-templated synthesis and in vitro selection. Nature. Sep. 30, 2004;431(7008):545-9. 30;431(7008):545-9.

* cited by examiner-

| substrates | | green:red fluorescence ratios | | DNA-templated yields (%) | | product consistent with observed mass |
| --- | --- | --- | --- | --- | --- | --- |
| | | 37°C | 25°C | 37°C | 25°C | |
| A5 (alkyne) | B5 (alkene) | 2.7 | 3.7 | 35 | 31 | R-CH2CH2-C(O)-CH=CH-CH2-R |
| A5 (alkyne) | B3 (acrylamide) | 3.5 | 3.1 | 28 | 20 | R-CH2CH2-C(O)-CH2CH2-C(O)NHR |
| A5 (alkyne) | B8 (arylboronic acid) | 1.6 | 1.9 | 36 | 34 | R-CH2-C≡C-C6H4-CH2-R |
| A5 (alkyne) | homocoupling | 2.6 | 2.7 | 45 | 42 | R-CH2CH2-C(O)-CH=CH-CH2CH2-R |
| A4 (alkene) | B8 | 3.0 | 2.8 | 57 | 39 | R-CH=C(Et)-C6H4-CH2-R |
| A8 (furan) | B8 | 1.8 | <1.2 | 30 | 10 | R-CH2CH2-furan-C6H4-CH2-R |
| A8 (furan) | B3 | 1.8 | <1.2 | 19 | <10 | |
| A7 (aryl iodide) | B3 | 3.6 | <1.2 | 39 | 14 | R-C6H4-CH=CH-C(O)NHR |

Figure 3

| entry | metal(s) | solvent | conditions | isolated yield |
|---|---|---|---|---|
| a | 1 equiv. Na$_2$PdCl$_4$ | 1 M NaCl in H$_2$O | 25 °C, 15 h | 86% |
| b | 5 mol % Na$_2$PdCl$_4$<br>1 equiv. CuCl$_2$ | 100 mM NaCl in H$_2$O | 25 °C, 2 h | 90% |
| c | 5 mol % Na$_2$PdCl$_4$<br>1 equiv. CuCl$_2$ | 9:1 THF:H$_2$O | 25 °C, 4 h | 91% |
| d | 15 mol % Na$_2$PdCl$_4$<br>1 atm O$_2$ | 9:1 THF:H$_2$O | 25 °C, 14 h | 73% |
| e | 1 equiv. CuCl$_2$ | 100 mM NaCl in H$_2$O | 25 °C, 4 h | 0% |
| f | 1 equiv. CuCl | 100 mM NaCl in H$_2$O | 25 °C, 4 h | 0% |

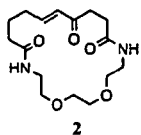
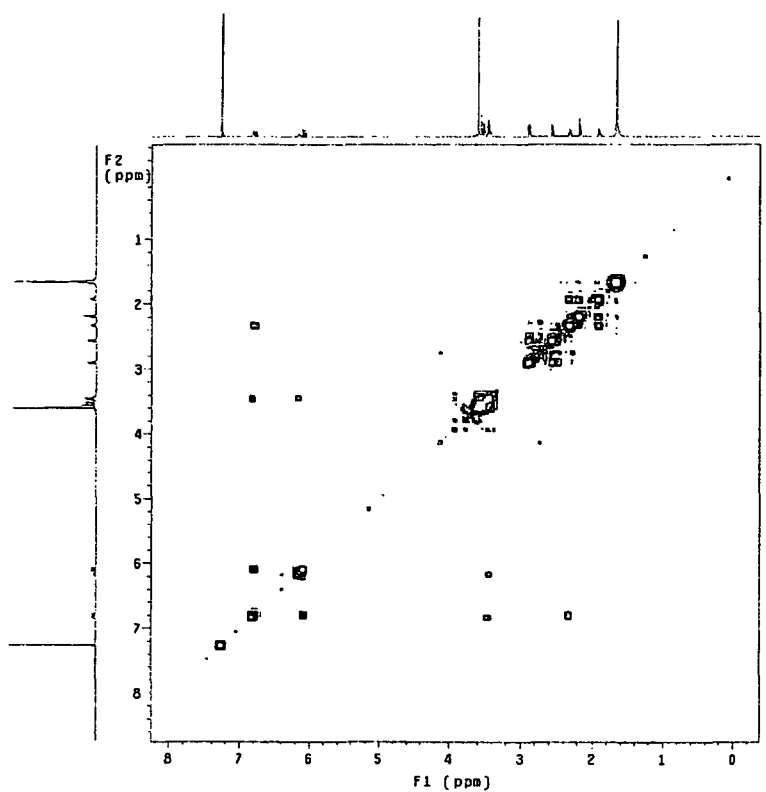
Figure 8

PALLADIUM-CATALYZED CARBON-CARBON BOND FORMING REACTIONS

RELATED APPLICATIONS

The present application claims priority under 35 U.S.C. §119(e) to U.S. provisional patent application, U.S. Ser. No. 60/602,255, filed Aug. 17, 2004, incorporated herein by reference.

GOVERNMENT SUPPORT

This invention was made with Government support under the National Institutes of Health award GM065865 and Office of Naval Research award N00014-03-1-0749. The Government has certain rights in the invention.

BACKGROUND OF THE INVENTION

Traditional approaches to reaction discovery typically focus on one particular chemical transformation. Predicted precursors for a target structure are chosen as substrates, and then particular reaction conditions are evaluated either manually or in a high-throughput format (Stambuli et al. Recent advances in the discovery of organometallic catalysts using high-throughput screening assays. *Curr. Opin. Chem. Biol.* 7, 420-426 (2003); Reetz,.. Combinatorial and evolution-based methods in the creation of enantioselective catalysts. *Angew. Chem. Int. Ed.* 40, 284-310 (2001); Stambuli et al. Screening of homogeneous catalysts by fluorescence resonance energy transfer. Identification of catalysts for room-temperature Heck reactions. *J. Am. Chem. Soc.* 123, 2677-8 (2001); Taylor et al. Thermographic selection of effective catalysts from an encoded polymer-bound library. *Science* 280, 267-70 (1998); Lober et al. Palladium-catalyzed hydroamination of 1,3-dienes: a calorimetric assay and enantioselective additions. *J. Am. Chem. Soc.* 123, 4366-7 (2001); Evans et al. Proton-activated fluorescence as a tool for simultaneous screening of combinatorial chemical reactions. *Curr. Opin. Chem. Biol.* 6, 333-338 (2002); each of which is incorporated herein by reference) for their ability to produce the desired product. Although this approach is very useful in addressing specific chemical problems, it does not lend itself to the discovery of entirely new chemical reactions. In fact, its focused nature may leave many areas of chemical reactivity unexplored.

A reaction discovery system capable of simultaneously evaluating in a single solution many combinations of substrates for their ability to form new bonds and covalent structures should optimally meet the following criteria: (1) the system should organize complex substrate mixtures into discrete pairs that can react (or not react) without affecting the reactivity of the other substrate pairs; (2) the system should include a general method for separating reactive substrate pairs from unreactive pairs; and (3) the reactive substrate pairs should be easily identifiable.

Recent developments in DNA-templated synthesis suggest that DNA annealing can organize many substrates in a single solution into DNA sequence-programmed pairs. DNA-templated synthesis and in vitro selection may, therefore, be used to evaluate many combinations of substrates and conditions for bond-forming reactions (Calderone et al. Directing otherwise incompatible reactions in a single solution by using DNA-templated organic synthesis. *Angew. Chem. Int. Ed.* 41, 4104-8 (2002); Gartner et al. The generality of DNA-templated synthesis as a basis for evolving non-natural small molecules. *J. Am. Chem. Soc.* 123, 6961-3 (2001); Gartner et al. Expanding the reaction scope of DNA-templated synthesis. *Angew. Chem. Int. Ed.* 41, 1796-1800 (2002); Rosenbaum et al. Efficient and Sequence-Specific DNA-Templated Polymerization of Peptide Nucleic Acid Aldehydes. *J. Am. Chem. Soc.* 125, 13924-5 (2003); each of which is incorporated herein by reference). See also published U.S. patent application 2004/018042, published Sep. 16, 2004, which is incorporated herein by reference. Watson-Crick base pairing controls the effective molarities of substrates tethered to DNA strands. Selection for bond formation, amplification by PCR, and DNA array analysis then reveals bond-forming substrate combinations and conditions. The versatility and efficiency of DNA-templated synthesis enables the discovery of reactions between substrates typically thought to be unreactive.

Therefore, DNA-templated synthesis may be used to discover new chemical reactions that are potentially broadly useful in the synthesis of chemical compounds such as pharmaceutical agents, new materials, polymers, catalysts, etc. In the art of organic synthesis, there remains a need for additional carbon-carbon bond forming reactions. DNA-templated chemistry may be used to discover chemical reactions to satisfy this need.

SUMMARY OF THE INVENTION

The present invention provides a novel palladium-mediated carbon-carbon bond forming methodology discovered using DNA-templated chemistry. The reaction couples an alkene with a alkyne to form an enone product in the presence of palladium (II) as shown in the exemplary scheme below:

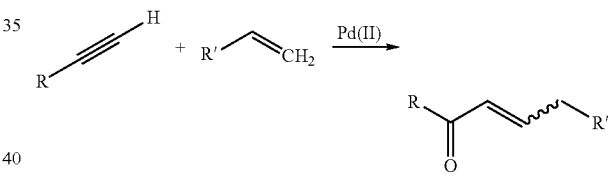

The reactions is mediated by either stoichiometric or catalytic quantities of palladium (II). Since the formation of an enone from an alkyne and alkene represents an oxidative coupling (see FIG. 11), the reaction may be catalyzed by palladium (II) in the presence of an oxidant to convert the Pd(0) generated by the reaction back to Pd(II). Possible oxidants useful in this reaction are $CuCl_2$, air, oxygen, benzoquinone, hydrogen peroxide, alkyl peroxides (e.g., tert-butyl hydroperoxide), etc. The reaction produces a trans-enone, cis-enone, or a mixture of stereoisomers depending on the reaction conditions and the reactants. Typically, the trans-enone is formed.

The alkynyl moiety undergoing reaction is a terminal alkyne because the reaction is thought to proceed by soft deprotonation of the terminal alkyne by the palladium (II). In certain embodiments, the alkenyl moiety undergoing reaction is a terminal alkenyl moiety. In other embodiments, both the alkenyl and alkynyl moieties are terminal alkenyl and alkynyl moieties. The akenyl and alkynyl moieties may be part of any chemical compound. The alkynyl moiety is frequently proximal (i.e., within 1 to 5 atoms) of a Lewis basic group.

The reaction may be an intermolecular or intramolecular reaction. The reaction is also useful in preparing cyclic enones as shown in the scheme below:

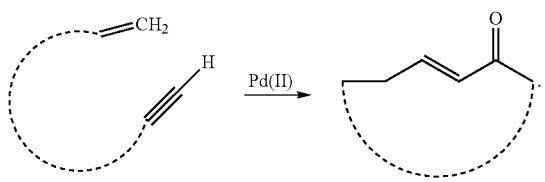

The reaction is particularly useful in preparing macrocyclic enones.

This new palladium-mediated coupling reaction is also useful in preparing trisubstituted enones of the formulae:

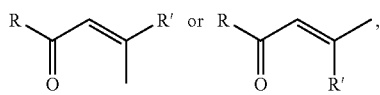

resulting from a different site of insertion.

The reaction may also be used to form enynes of the formula:

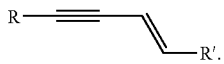

The enyne product is thought to be an intermediate in the formation of the enone. The enyne may be formed under conditions with limited Pd(II), lack of sufficient oxidant, and/or reduced amounts of water in the reaction mixture.

The reactions of the invention are typically performed in an aqueous medium or in a water-miscible solvent with at least 10% water. The reactions is typically performed at approximately 25° C. or room temperature for 2-15 hours with slow addition of the reactants or the alkyne to a solution of Pd(II). In certain embodiments, an acid (e.g., NaHSO$_4$, TFA, TCA) or salt (e.g., NaCl) is added to the reaction mixture.

The reactions of the present invention may be performed in a DNA-templated format or a non-DNA-templated format. Preferably, the reaction is performed in a non-DNA-templated format. As will be appreciated by one of skill in this art, the DNA-templated format may use other nucleic acids besides DNA, for example, RNA, DNA-RNA hybrids, or DNA or RNA analogs.

Although other enone-forming coupling reactions such as the Horner-Wadsworth-Emmons reaction and aldol condensation are known, the mild reaction conditions, simple hydrocarbon starting materials, and high efficiency of this new reaction render it an attractive alternative to these other well known reactions. This new enone-forming reaction may be particularly useful in preparing macrocyclic enones, of which there are numerous known biologically active examples (Staunton et al. Polyketide biosynthesis: a millennium review. *Nat. Prod. Rep.* 18, 380-416 (2001); incorporated herein by reference).

The invention further provides substrates (e.g., alkenes, alkynes, etc.), reagents, solvents, catalysts, ligands, oxidants, kits, and instructions for performing the novel palladium-mediated alkene-alkyne coupling reaction.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books (Sausalito, Calif.), 1999; and Kemp and Vellaccio, *Organic Chemistry*, Worth Publishers, Inc. (New York), 1980; the entire contents of which are incorporated herein by reference.

Certain compounds useful in the present invention or produced by the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be contemplated in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3,98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized.

Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-1-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2- dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1- dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), βtrimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the methods of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds. The term "stable", as used herein, preferably refers to compounds which possess stability sufficient to allow manufacture and which maintain the integrity of the compound for a sufficient period of time to be detected and preferably for a sufficient period of time to be useful for their desired purposes.

The term "aliphaticm," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. In certain embodiments, monosubstituted alkenyl moieties are preferred as reactants in the inventive reactions. In other embodiments, disubstituted or trisubstituted alkenyl moieties may be used in the inventive reactions. In certain embodiments, the alkenyl moiety useful in the inventive reaction is a terminal alkenyl moiety. In certain embodiments, the alkene is a monosubstituted terminal alkene. In other embodiments, the alkene is a disubstituted terminal alkene. Representative alkynyl groups include, but are not limited to, ethynyl, 2-propynyl (propargyl), 1-propynyl, and the like. In certain embodiments, the alkynyl moiety useful in the synthetic methodology of the present invention is a terminal alkynyl moiety.

The term "alkoxy", or "thioalkyl" as used herein refers to an alkyl group, as previously defined, attached to the parent molecule through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x$ (CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl," as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2$ $R_x$; —$NR_x$(CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "enone," as used herein refers to a conjugated system of an alkene and a ketone (e.g., $R_2C$=CR—CO—R). The alkene portion of the enone may be in the cis- or trans-configuration. In certain embodiments, the enone is disubstituted. In other embodiments, the enone is trisubstituted. The enone may be part of a cyclic structure. In certain embodiments, the enone is part of a macrocyclic structure.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2R_x$; —$NR_x$, (CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle," as used herein, refers to a non-aromatic 5-, 6-, or 7- membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2R_x$; —$NR_x$(CO)$R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples which are described herein.

The term "carbocycle," as used herein, refers to an aromatic or non-aromatic ring in which each atom of the ring is a carbon atom.

The term "independently selected" is used herein to indicate that the R groups can be identical or different.

As used herein, the term "labeled" is intended to mean that a compound has at least one element, isotope, or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position of the compound.

Definitions of non-chemical terms used throughout the specification include:

"Nucleic acid": Nucleic acid refers to a polymer of nucleotides. Typically, a nucleic acid comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C-5 propynyl-cytidine, 2-aminoadenosine, C5-bromouridine, C5-fluorouridine, C5-iodouridine, C5-propynyl-uridine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5-N-phosphoramidite linkages).

BRIEF DESCRIPTION OF THE DRAWING

FIG. 3 shows the characterization in a DNA-templated format of array positives resulting from exposure to 500 μM $Na_2PdCl_4$ at 37° C. for 1 h, or at 25° C. for 20 min. Putative reactions were screened by PAGE and MALDI-TOF mass spectroscopic analysis (Supplementary Information). Template architectures and reaction conditions were chosen to match those used in the selection rather than to maximize product yields. Product structures other than those proposed are possible. The green:red fluorescence ratio for the internal standard at 37° C. and 25° C. is 2.9 and 3.5, respectively. For A8+B3, reactivity was not sufficient to obtain reliable product mass characterization.

FIG. 8 shows the homonuclear COSY spectrum of a macrocyclic trans-enone product.

DETAILED DESCRIPTION OF CERTAIN PREFERRED EMBODIMENTS OF THE INVENTION

Figure 1:
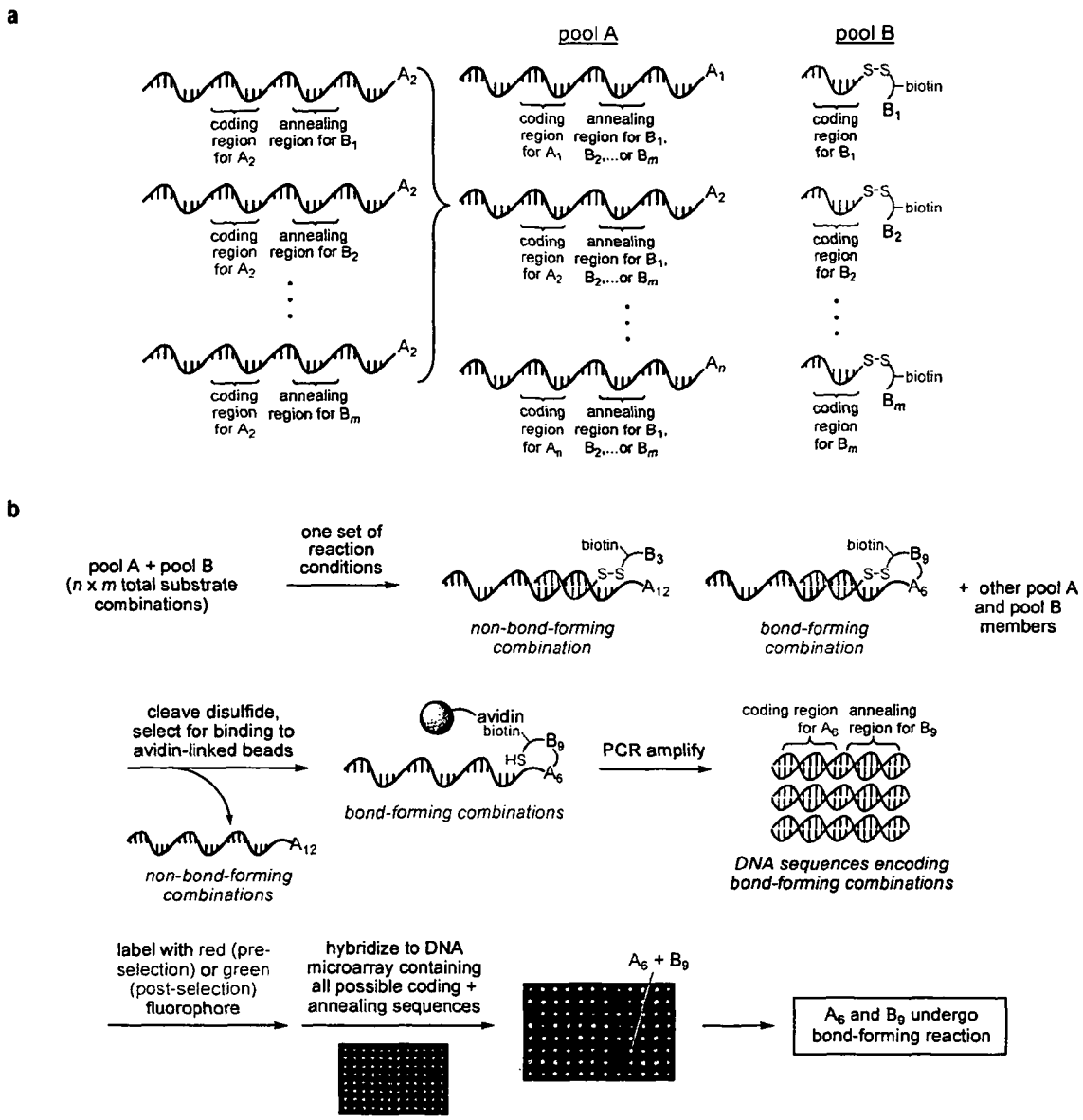
FIG. 1 shows the elements of a new approach to reaction discovery. a, Two pools of DNA-linked organic functional groups that associate each of n×m substrate combinations with a unique DNA sequence. b, A general one-pot selection and analysis method for the detection of bond-forming reactions between DNA-linked substrates.

DNA-templated chemistry has been used to discover a new carbon-carbon bond forming reaction. This new synthetic methodology involves the palladium-mediated oxidative coupling of an alkyne and an alkene to form an enone. The reaction may be intramolecular to form a cyclic structure, or intermolecular to join two chemical compounds through a carbon-carbon bond. The basic reaction is shown in the exemplary scheme below:

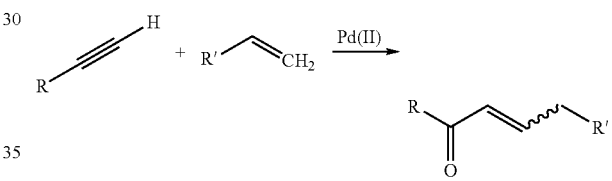

The reaction is typically performed with a terminal alkene and a terminal alkyne; however, a terminal alkyne is not necessary to achieve reaction. Typically, monosubstituted alkenes are used in the reaction; however, disubstituted alkene may also be used. The resulting di-substituted enone may be in the cis- or trans-configuration, or the reaction may result in a mixture of the two. The thermodynamically more favorable trans-configuration is generally preferred.

The reactive alkynyl moiety is a terminal alkyne of the formula:

wherein R is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —C(═O)$R_A$; —CO$_2R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, R is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl. In other embodiments, R is cyclic or acyclic, substituted or unsubstituted, branched or unbranched aliphatic; or cyclic or acyclic, substituted or unsubstituted, branched or unbranched heteroaliphatic. In yet other embodiments, R is substituted or unsubstitued, branched or unbranched aryl (e.g., phenyl). In other embodiments, R is substituted or unsubstituted, branched or unbranched heteroaryl (e.g., pyridinyl). Essentially, the alkynyl moiety may be part of any chemical compound and be useful in the inventive reaction. In certain embodiments, other reactive groups on the compound with the alkyne moiety may be protected or masked.

In certain embodiments, the alkynyl moiety used in the inventive reaction is proximal to a Lewis basic or electron rich functional group such as an amide, ester, amine, imine, ether, thioether, carbamate, urea, carbonate, hydroxyl, thiol, or ketone. In certain embodiments, the alkynyl moiety is proximal to an amide group. For example, alkynes of the formula:

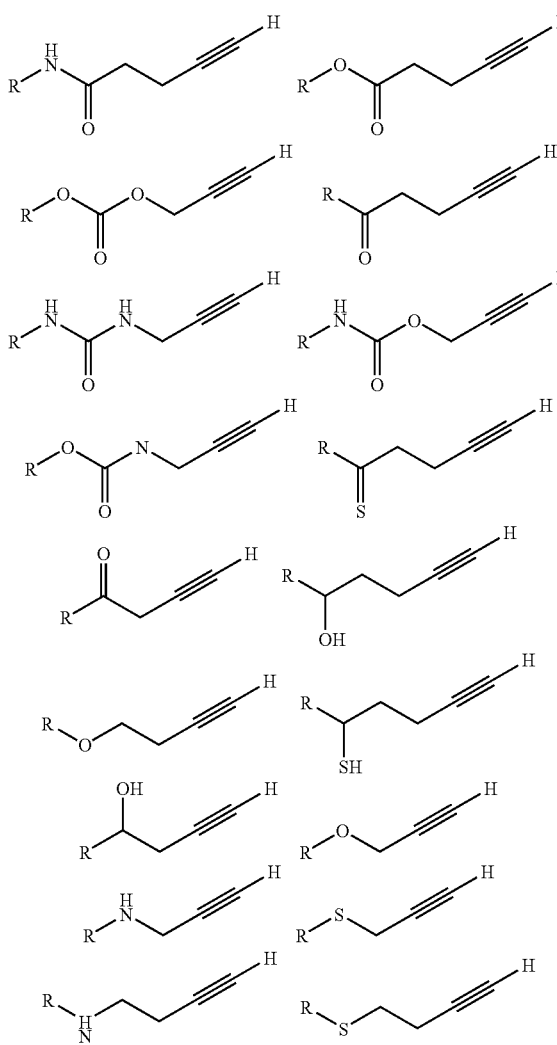

are useful in the inventive reaction

Figure 11:
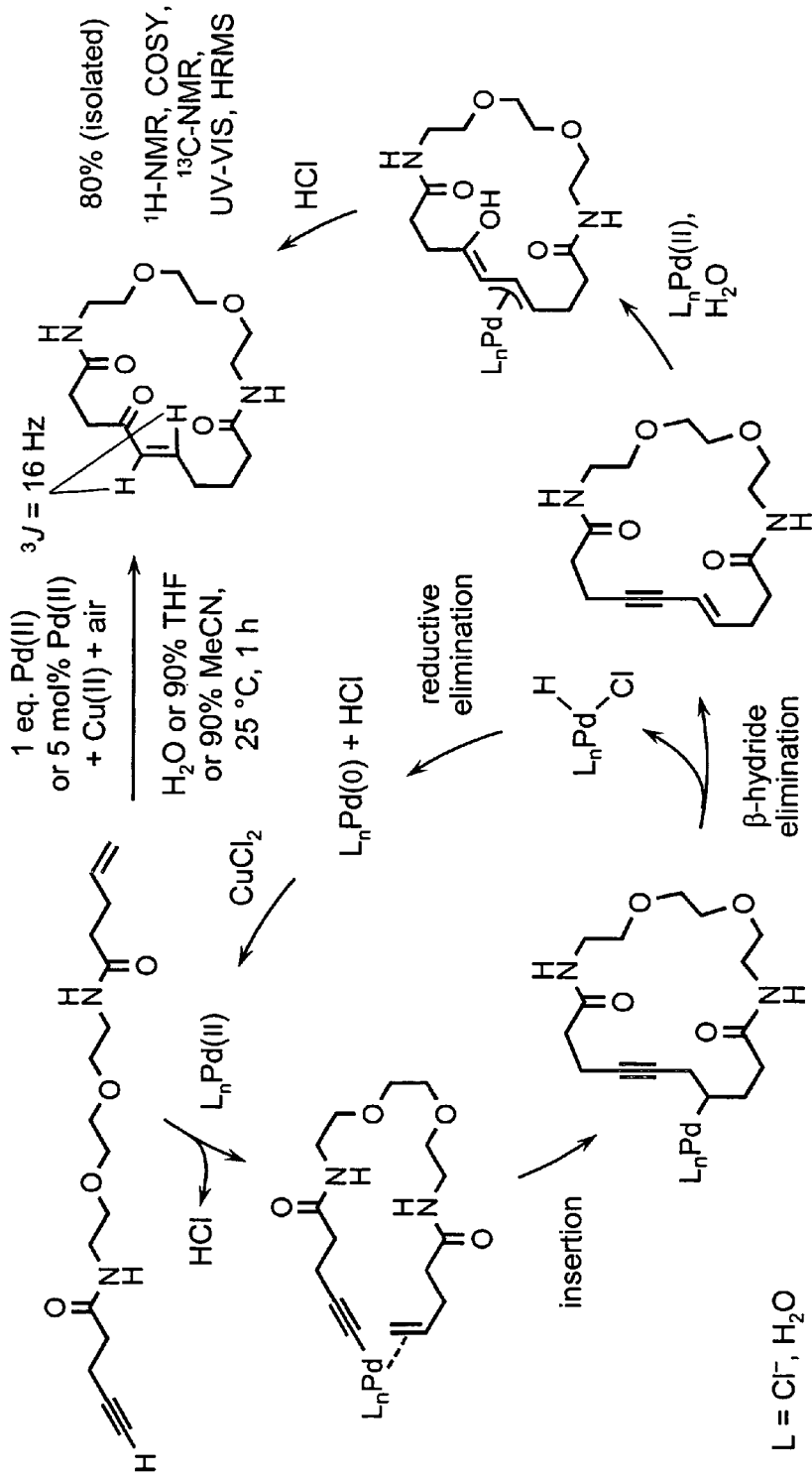
FIG. 11 shows a proposed mechanism for the palladium-mediated alkyne-alkene coupling reaction.
Figure 12:
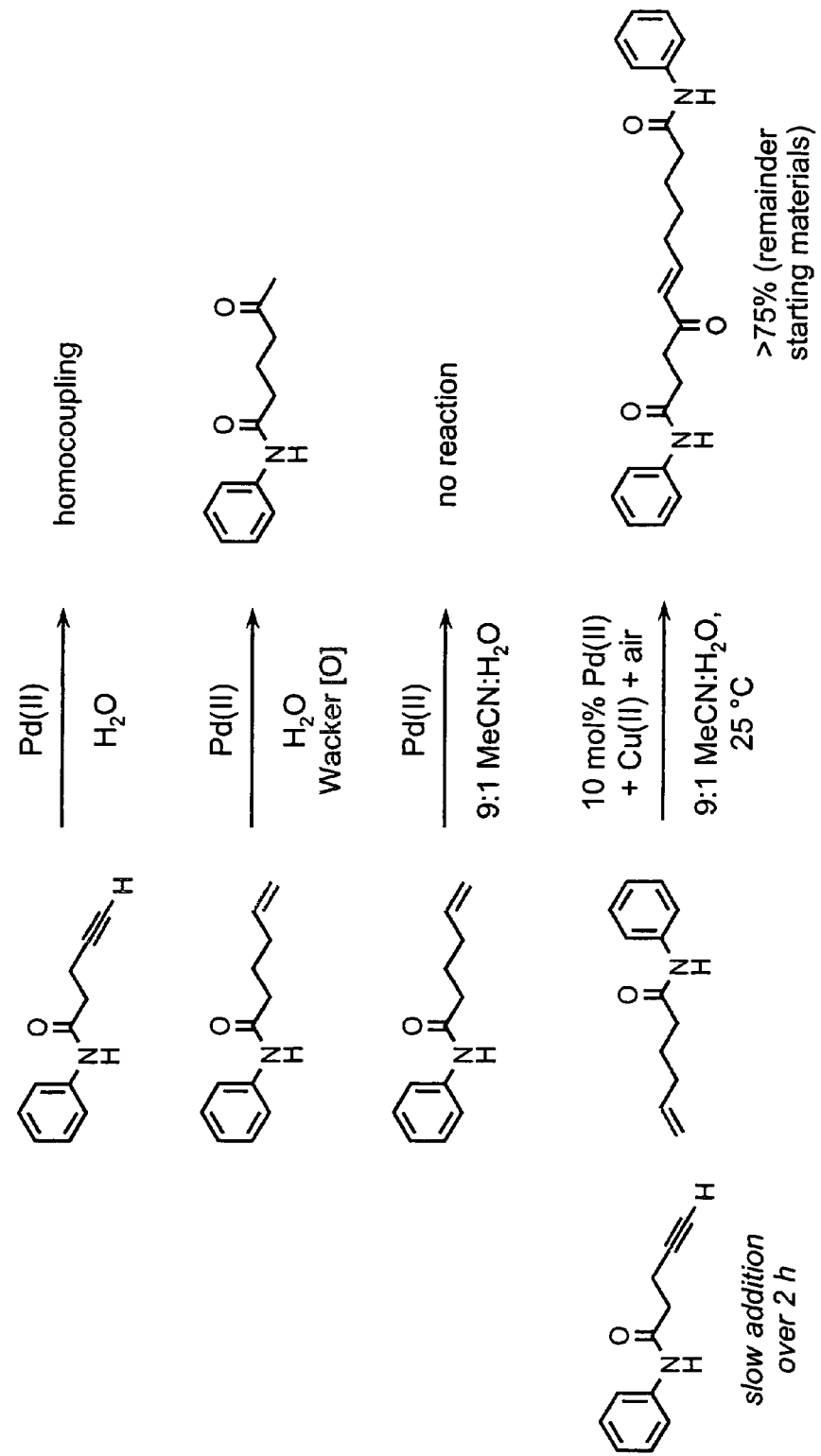
FIG. 12 shows intermolecular non-DNA-templated alkyne-alkene coupling reactions.

Without wishing to be bound by any particular theory, the Lewis basic group is thought to deliver the metal Pd(II) to the alkyne to initiate the reaction. The reaction is thought to proceed through a Pd-alkynyl intermediate where the C—H of the alkynyl moiety is replaced with a C—Pd bond (see FIG. 11). In certain embodiments, the Lewis basic group and alkyne are only separated by 1 to 5 atoms, preferably 1 to 3, and most preferably just 1 or 2 atoms. In certain embodiments, the atoms separating the Lewis basic group from the alkynyl moiety are unsubstituted carbon atoms. In other embodiments, the carbon atoms may be substituted. In yet other embodiments, the atoms separating the Lewis basic group from the alkynyl moiety are carbons atoms and heteroatoms (e.g., S, O, or N). Without a Lewis basic functional group proximal to the alkynyl moiety, the yield of the reaction is decreased (e.g., from 80-90% yields to 40-50% yields); however, at least some of the desired product is formed. For certain applications, these decreased yields may be acceptable. Also, as would be appreciated by one of skill in this art, the reaction conditions may be optimized to increase the yield of the reaction. Such reaction parameters as solvent, temperature, duration of reaction, salt concentration, pH, water concentration, work-up, etc. may all affect yield In certain embodiments, the alkyne is of the formula:

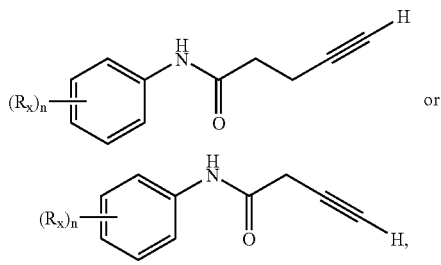

wherein each occurrence of $R_X$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_x'$; =O; —C(=O)$R_x'$; —$CO_2R_x'$; —CN; —SCN; —$SR_x'$; —$SOR_x'$; —$SO_2R_x'$; —$NO_2$; —N($R_x'$)$_2$; —NHC(O)$R_x'$; or —C($R_x'$)$_3$; wherein each occurrence of $R_X'$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and n is an integer between 0 and 5. In certain embodiments, n is 0. In other embodiments, n is 1. In yet other embodiments, n is 2. In still further embodiments, n is 3, 4, or 5.

Alkenyl moieties useful in the inventive reaction may be any type of substituted or unsubstituted alkenyl moiety. In certain embodiments, the alkenyl moiety is monosubstituted. In other embodiments, the alkenyl moiety is disubstituted. In yet other embodiments, the alkneyl moiety is trisubstituted. The alkenyl moiety may be substituted with one, two or three aliphatic, heteroaliphatic, cyclic, acyclic, acyl, aryl, or heteroaryl group, or combination thereof. In certain embodiments, the alkenyl moiety is a terminal alkene of the formula:

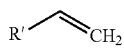

wherein R' is hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, R' is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl. In other embodiments, R' is cyclic or acyclic, substituted or unsubstituted, branched or unbranched aliphatic; or cyclic or acyclic, substituted or unsubstituted, branched or unbranched heteroaliphatic. In yet other embodiments, R' is substituted or unsubstitued, branched or unbranched aryl (e.g., phenyl).

In other embodiments, R' is substituted or unsubstituted, branched or unbranched heteroaryl (e.g., pyridinyl). In certain embodiments, the alkenyl moiety is a disubstituted terminal alkene of the formula:

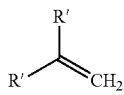

wherein each occurrence of R' is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl; —$OR_A$; =O; —C(=O)$R_A$; —$CO_2R_A$; —CN; —SCN; —$SR_A$; —$SOR_A$; —$SO_2R_A$; —$NO_2$; —N($R_A$)$_2$; —NHC(O)$R_A$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, R' is cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstitued, branched or unbranched aryl; substituted or unsubstituted, branched or unbranched heteroaryl. In other embodiments, R' is cyclic or acyclic, substituted or unsubstituted, branched or unbranched aliphatic; or cyclic or acyclic, substituted or unsubstituted, branched or unbranched heteroaliphatic. In yet other embodiments, R' is substituted or unsubstitued, branched or unbranched aryl (e.g., phenyl). In other embodiments, R' is substituted or unsubstituted, branched or unbranched heteroaryl (e.g., pyridinyl).

Essentially, the alkenyl moiety may be part of any chemical compound and be useful in the inventive reaction. In certain embodiments, other reactive groups on the compound with the alkenyl moiety may be protected or masked. Unlike the alkynyl moiety, the alkenyl moiety does not require a Lewis basic moiety proximal to the alkene.

In certain embodiments, the alkenyl and alkynyl moieties are part of one molecule resulting in an intramolecular reaction as shown in the exemplary scheme:

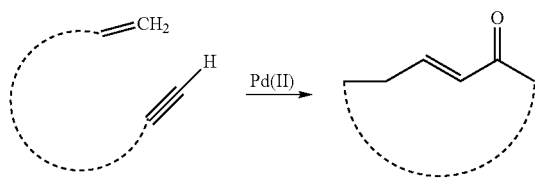

The inventive reaction results in the formation of a cyclic enone. The resulting cyclic enone is 6-membered up to 40-membered. In certain embodiments, the resulting cyclic enone is 10-membered to 25-membered, 8-membered to 30-membered, 12-membered to 20-membered, or 12-membered to 30-membered. In certain embodiments, a 6-membered, 7-membered, 8-membered, 9-membered, 10-membered, 11-membered, 12-membered, 13-membered, 14-membered, 15-membered, 16-membered, 17-membered, 18-membered, 19-membered, 20-membered, 21-membered, or 22-membered cyclic enone is formed using the inventive reaction. In certain low-membered ring systems (e.g., 4-, 5-, 6-, or 7-membered cyclic enones), the trans-configuration of the enone may be disfavored as compared to the cis-configuration. In certain embodiments, the substrate for macrocyclization is:

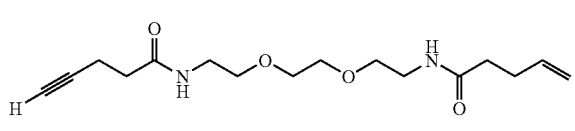

The polyethylene glycol linker between the amide groups may be replace with an substituted or unsubstituted, cyclic or acyclic aliphatic or heteroaliphatic chain. As discussed above, the alkynyl moiety of the substrate is preferably proximal to a Lewis basic group such as an amide.

In certain embodiments, an enone of the formula:

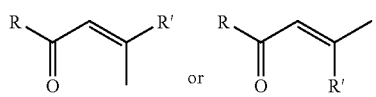

is formed. The trisubstituted alkene may be the result of insertion of Pd(II) at a different site than usual. This trisubstituted product may be a side product under certain reaction conditions. The addition of a weak acid such as $NaHSO_4$ or TFA reduces the formation of the trisubstituted enone. As will be appreciated by one of skill in this art, the reaction conditions may be optimized for the production of the trisubstituted product. For example, certain alkene substrates may lead to the trisubstituted product, or the lack of an acid may increase the formation of the trisubstituted product.

Under certain reaction conditions rather than proceeding to the enone, an enyne of the formula

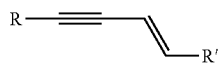

is formed. Condition that favor enyne formation include low concentration of palladium (II), low concentration of oxidant, lack of water, precipitation of Pd(0), not adding the substrate slowly to a solution of Pd(II), etc.

The reaction is mediate by palladium (II). Any source of palladium (II) may be used in the inventive reaction. Examples of sources of Pd(II) include $PdCl_2$, $PdSO_4$, and $Na_2PdCl_4$. Palladium (0) in conjunction with an oxidant may also be used. In certain embodiments, a stoichiometric amount of palladium (II) is used. For example, 1, 1.1, 1.2, 1.5, or 2 equivalents of Pd(II) may be used. In other embodiments, the reaction is catalyzed by palladium (II). The palladium may be 1-15 mol %, preferably 5-10 mol %. In certain embodiments, approximately 5 mol % palladium(II) is used. In other embodiments, approximately 10 mol % palladium (II) is used. In yet other embodiments, approximately 15 mol % palladium (II) is used. If palladium is used as a catalyst, a stoichiometric oxidant must be used to convert the Pd(0) generated by the oxidative coupling back to Pd(II). Any oxidant known in the art may be used. Examples of useful oxidants in the inventive catalytic reaction include $CuCl_2$, air, $O_2$, hydrogen peroxide, alkyl hydroperoxide (e.g., tert-butyl hydroperoxide), or benzoquinone.

The coupling reaction is typically performed by adding the substrates to a solution of the palladium(II). In certain embodiments, the reaction is performed by slowly adding the substrate(s) to a solution of Pd(II). In certain intermolecular reactions, the alkyne is added to a solution of the alkene and palladium (II). If the substrate is added too quickly, significant quantities of enyne are formed. Exposing the enyne to more palladium (II) does result in the production of the corresponding enone. The substrate(s) may be added over the course of 1-12 hours, preferably 1-6 hours, or more preferably from 2-4 hours. In certain embodiments, the addition proceeds over approximately 2 hours. In other embodiments, the addition proceeds over approximately 3 hours. In still other embodiments, the addition proceeds over approximately 4 hours. In yet other embodiments, the additions proceeds over approximately 5 hours.

The inventive reaction typically proceeds to form the trans-enone. However, reactions conditions may be altered to afford the cis-enone or a mixture of cis- and trans-enones. For example, in an intramolecular reaction, the resulting ring size may be small enough to disfavor the trans-enone. In certain embodiments, an enyne intermediate is formed and may be isolated. The enyne may also be subsequently converted to enone with the addition of more palladium (II).

The reaction may be performed in a variety of organic solvents. Typically, some water is present. In certain embodiments, an aqueous salt solution is used as the solvent. The concentrations of salt may range from 0.001 M to 1 M. Any salt may be used. Examples of salts useful in the inventive reaction include NaCl, KCl, NaBr, KBr, etc. In certain embodiments, fluoride anion or iodide anion is not included in the reaction mixture. In certain embodiments, the reaction is run in an aqueous 1 M NaCl. In other embodiments, the reaction is run in aqueous 100 mM NaCl. Organic solvents useful in the inventive reaction include ethers (e.g., THF, diethyl ether), alcohols (e.g., methanol, ethanol, isopropanol), halogenated solvents, benzene, toluene, etc. In other embodiments, THF is used, for example, 9:1 THF/$H_2O$. In yet other embodiments, aceonitrile is used, for example, 90% acetonitrile, 80% acetonitrile, 70% acetonitrile, 60% acetonitrile, or 50% acetonitrile. Preferably, if an organic solvent is used, water is at least miscible with the organic solvent up to 10%, 15%, 20%, 25%, 30%, 35%, 40%, 50%, etc. In certain embodiments, at least 5%, 10%, 15%, or 20% of the solvent is water. In other embodiments, no water is present in the reaction mixture. In other embodiments, an alcohol is used in place of water. For example, methanol, ethanol, isopropanol, butanol, etc. may be used in the reaction mixture. Alcohols are particularly useful if a non-water miscible solvent such as diethyl ether or toluene is used for the reaction.

In certain embodiments, an acid is added to the reaction mixture. Weak acids which have been shown to be particularly useful in the present invention include trifluoroacetic acid (TFA), trichloroacetic acid (TCA), and $NaHSO_4$. Stronger acids such as HCl, $H_2SO_4$, etc. may be used if the substrates tolerate strong acid. Approximately 0.5 equivalents to approximately 2 equivalents of acid may be used in the reaction mixture. In certain embodiments, approximately 0.5 equivalents are used. In other embodiments, approximately 1 equivalent is used. In yet other embodiments, 1.5 equivalents are used. In the case of simple monosubstituted alkenes, the trisubstituted enone is formed in larger amounts if the acid is omitted from the reaction mixture.

The reaction is typically run at approximately room temperature from 1 hour to 20 hours. In certain embodiments, the reaction is run at a temperature between 15° C. and 35° C. The optimal temperature for running the reaction may be determined empirically. In certain embodiments, the temperature is between 20° C. and 30° C. In other embodiments, the reaction is run at approximately 25° C. The reaction duration may be determined empirically by monitoring the progress of the reaction (e.g., by TLC). In certain embodiments, the reaction may proceed for 1 hour, 2 hours, 4 hours, 6 hours, 10 hours, 12 hours, 13 hours, 14 hours, or 15 hours. In certain embodiments, the reaction may be stopped as soon as the slow addition of the substrate is finished. In other embodiments, the reaction may be continued for another 1-5 hours after all the substrate has been added. The reaction may be followed by an analytical technique such as TLC to determine when the reaction should be stopped (e.g., when all the limiting reactant has been converted to product).

In certain embodiments, the reaction is not nucleic acid- or DNA-templated. Preferably, the reaction proceeds in the absence of a nucleic acid such as RNA or DNA. In other embodiments, the reaction may be DNA-templated.

The invention further provides substrates (e.g., alkenes, alkynes, etc.), reagents, solvents, catalysts, ligands, oxidants, kits, and instructions for performing the novel palladium-mediated alkene-alkyne coupling reaction. The substrates include alkenyl or alkynyl moieties as described herein for coupling to an alkyne or alkene, respectively. These substrates may be provided in a kit for convenience. The kit may also include instruction for performing the inventive reaction. Solvents, salts, and acids for use in the inventive reaction may also be in a kit. The palladium reagent such as a palladium salt may also be provided. Suitable ligands for the palladium metal are also optionally provided. In certain embodiments in which catalytic quantities of palladium (II) are used, the kit may include an oxidant such as a copper salt, benzoquninone, etc. In certain embodiments, the kit may include one or more alkenes for use in the inventive reaction. In other embodiments, the kit may include one or more alkynes for use in the inventive reaction.

The discovery of this new carbon-carbon bond forming reaction broadly useful in the synthesis of organic molecules illustrates the powerfulness of DNA-templated synthesis. The techniques of DNA-templated synthesis and in vitro selection have allowed for the discovery of a new chemical methodology applicable outside the DNA-templated realm. The inventive palladium-mediate alkene-alkyne coupling reaction may be used in the synthesis of any organic molecule containing an enone moiety or a molecule derived from an enone. The reaction is particularly useful given its very mild reaction conditions, high efficiency, and compatibility with water. The reaction is particularly useful in preparing natural products or natural product-like molecules with an enone structure. The synthesis of macrocyclic enones (Staunton et al. Polyketide biosynthesis: a millennium review. *Nat. Prod. Rep.* 18, 380-416 (2001); incorporated herein by reference) is particularly amenable to the inventive methodology.

These and other aspects of the present invention will be further appreciated upon consideration of the following Examples, which are intended to illustrate certain particular embodiments of the invention but are not intended to limit its scope, as defined by the claims.

EXAMPLES

Example 1

Reaction Discovery Enabled by DNA-Templated Synthesis and In Vitro Selection

Recent developments in DNA-templated organic synthesis (Calderone, C. T., Puckett, J. W., Gartner, Z. J. & Liu, D. R. Directing otherwise incompatible reactions in a single solution by using DNA-templated organic synthesis. *Angew. Chem. Int. Ed.* 41, 4104-8 (2002); Gartner, Z. J. & Liu, D. R. The generality of DNA-templated synthesis as a basis for evolving non-natural small molecules. *J. Am. Chem. Soc.* 123, 6961-3 (2001); Gartner, Z. J., Kanan, M. W. & Liu, D. R. Expanding the reaction scope of DNA-templated synthesis. *Angew. Chem. Int. Ed.* 41, 1796-1800 (2002); Rosenbaum, D. M. & Liu, D. R. Efficient and Sequence-Specific DNA-Templated Polymerization of Peptide Nucleic Acid Aldehydes. *J. Am. Chem. Soc.* 125, 13924-5 (2003); each of which is incorporated herein by reference) suggest that DNA annealing can organize many substrates in a single solution into DNA sequence-programmed pairs. To this end, we prepared two pools of DNA-linked substrates, with n substrates in pool A and m substrates in pool B. Each substrate in pool A is covalently linked to the 5' end of a set of DNA oligonucleotides containing one "coding region" (uniquely identifying that substrate) and one of m different "annealing regions" (FIG. 1a). Each of the m substrates in pool B is attached to the 3' end of an oligonucleotide carrying a coding region that uniquely identifies the substrate and that complements one of the m annealing regions in pool A.

When pools A and B are combined in a single aqueous solution at nanomolar concentrations, Watson-Crick base pairing organizes the mixture into n×m discrete pairs of substrates attached to complementary sequences. Only substrates linked to complementary oligonucleotides experience effective molarities in the millimolar range (Gartner et al. The generality of DNA-templated synthesis as a basis for evolving non-natural small molecules. *J. Am. Chem. Soc.* 123, 6961-3 (2001); incorporated herein by reference); substrates linked to non-complementary oligonucleotides experience nanomolar solution concentrations and hence do not react with each other at a significant rate. This effective molarity-based design enables reactions that could be suppressed by preferential dimerization of one or both substrates. The possibility of interference by the structure of DNA during reactions between substrates is minimized by using long and flexible substrate-DNA linkers (Li et al. Stereoselectivity in DNA-templated organic synthesis and its origins. *J. Am. Chem. Soc.* 125, 10188-9 (2003); incorporated herein by reference).

The separation of reactive pairs of substrates is based on selection concepts used in the directed evolution of catalytic RNA and DNA (Wilson et al. In vitro selection of functional nucleic acids. *Annu. Rev. Biochem.* 68, 611-647 (1999); Joyce, Directed evolution of nucleic acid enzymes. *Annu. Rev. Biochem.* 73, 791-836 (2004); each of which is incorporated herein by reference) (FIG. 1b). We covalently linked each pool B substrate to its corresponding oligonucleotide by a linker that contains a biotin group and a disulfide bond (FIG. 1b and Experimentals). After incubation under a set of chosen reaction conditions, followed by cleavage of the disulfide bonds, only pool A sequences encoding bond formation between a pool A and pool B substrate remain covalently linked to biotin. Streptavidin affinity selection of the resulting solution separates biotinylated from non-biotinylated sequences. In contrast to many existing reaction discovery screens (Lober, O., Kawatsura, M. & Hartwig, J. F. Palladium-catalyzed hydroamination of 1,3-dienes: a calorimetric assay and enantioselective additions. *J. Am. Chem. Soc.* 123, 4366-7 (2001); incorporated herein by reference) focused on identifying desired products or efficient catalysts for desired reaction types, our selection-based approach does not depend on any specific substrate or product property but instead can identify all substrate pairs capable of forming a covalent bond under the reaction conditions.

Reactive substrate pairs are identified by PCR amplification of the selected sequences followed by DNA microarray analysis (vide infra). The ratio and location of fluorescence on the resulting array reveals the identity of substrates that have undergone a bond-forming reaction. Because PCR amplification is extremely sensitive, femtomole quantities of substrates are sufficient for the entire reaction discovery process.

Figure 2:
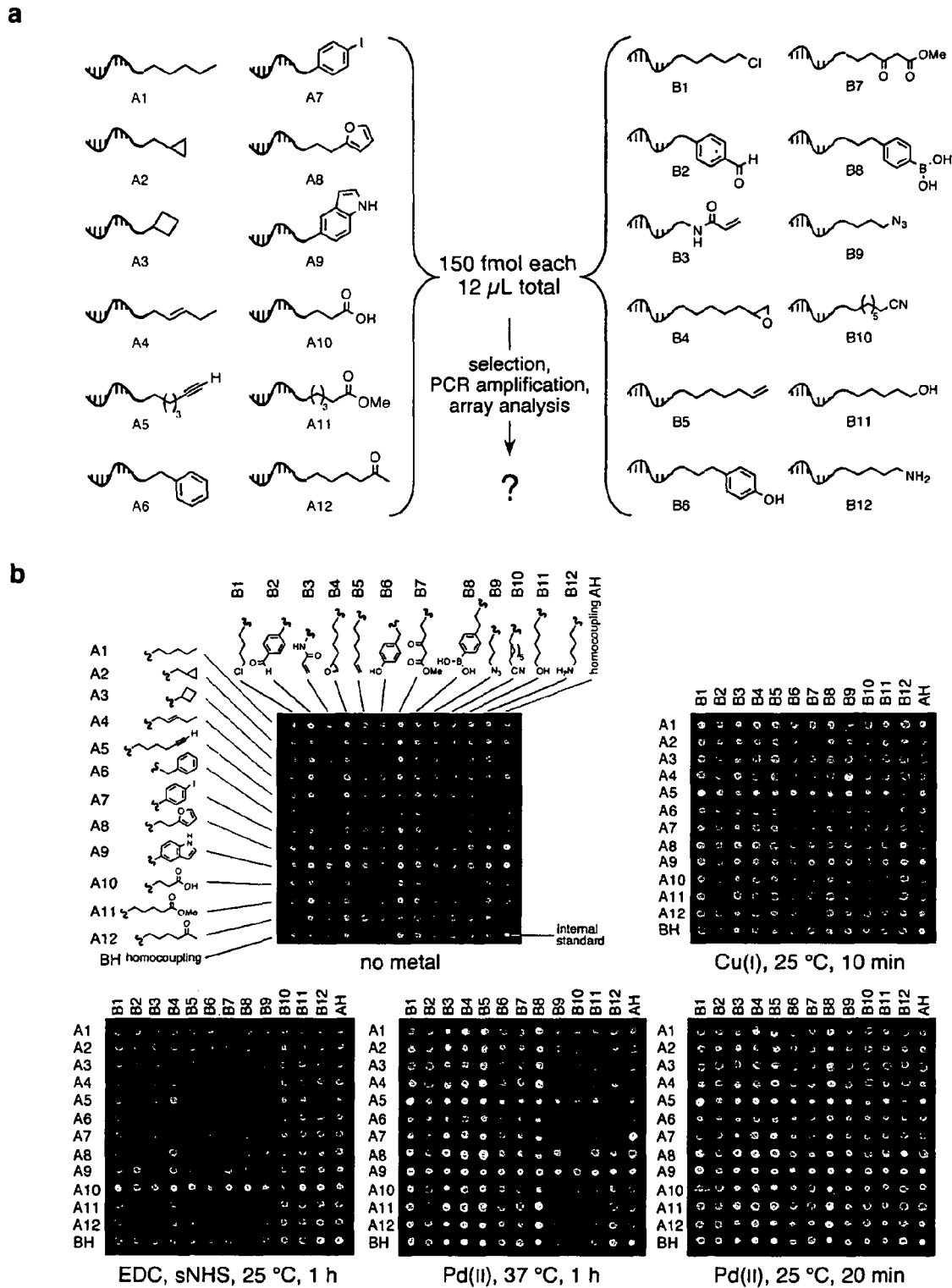
FIG. 2 shows the results from reaction discovery selections and analysis. a, Pool A and pool B substrates used in this work. b, Qualitative results of reaction discovery selections after exposure to the reaction conditions listed below each array image. Spots that are significantly green suggest bond formation between the corresponding substrates (quantitative fluorescence ratios in the Supplementary Data are used for actual interpretations). The 840 reaction possibilities in these five experiments were evaluated by one researcher in two days. See the Supplementary Methods for detailed reaction conditions.
Figure 5:
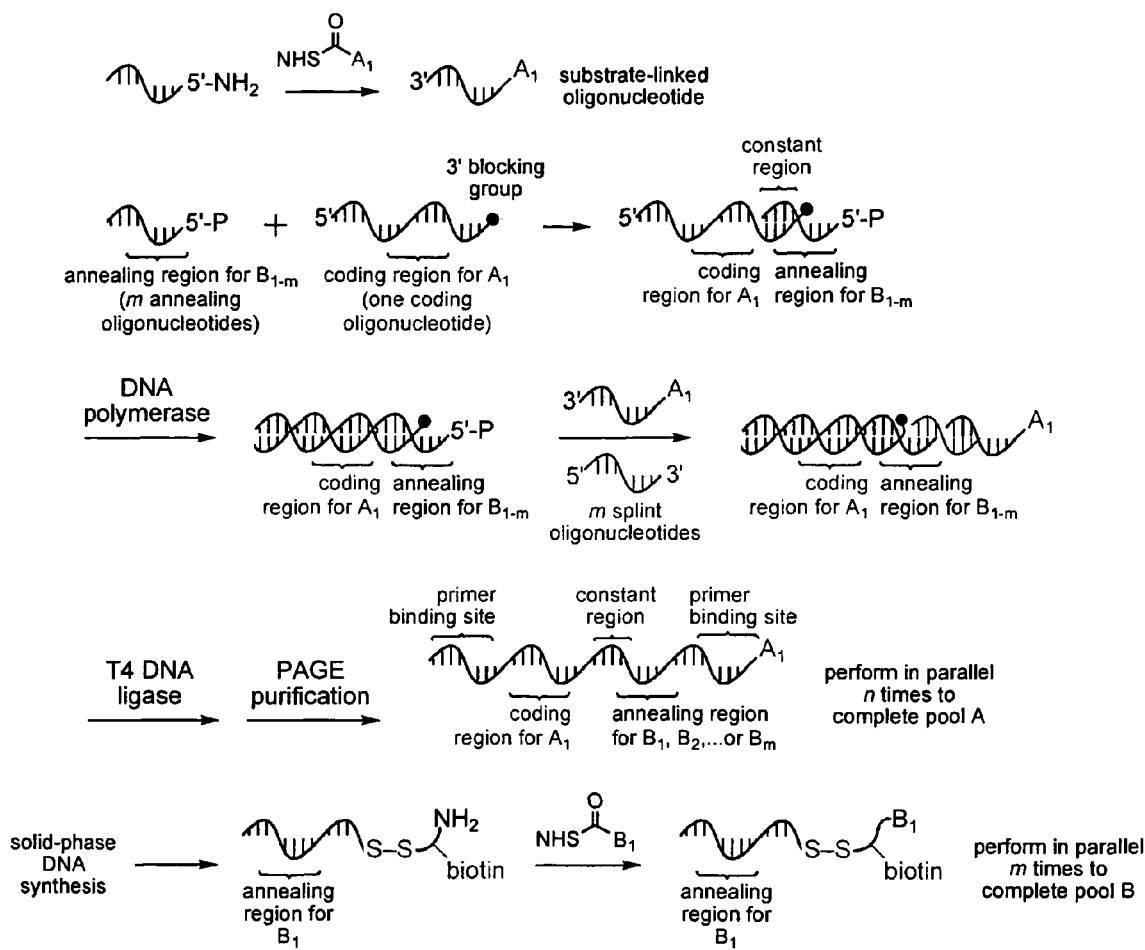
FIG. 5 shows the assembly of pool A and pool B DNA-linked substrates for reaction discovery enabled by DNA-templated chemistry.

We prepared pool A and pool B containing 12 substrates each (FIG. 2a), representing 144 heterocoupling combinations (see Experimentals and FIG. 5 for details). We also prepared DNA-linked substrates to enable detection of homocoupling of any of the 24 different substrates, bringing the total number of unique substrate combinations to 168 (FIG. 2a). The 24 substrates in FIG. 2a were chosen to represent simple functional groups commonly encountered in organic molecules. New reactions forming bonds between simple functionalities are of special interest because they may provide more accessible alternatives to coupling reactions that require more complex substrates. Although our approach requires the preparation of DNA-linked substrates, a single nmol-scale preparation of each pool provided sufficient material for >1,000 reaction discovery experiments that can collectively evaluate >168,000 combinations of substrates and reaction conditions.

To test the ability of our system to detect a single reactive combination of substrates out of 168 possibilities, we combined pool A and pool B in the presence of Cu(I), conditions that are known to promote a cycloaddition between a terminal alkyne (A5 in FIG. 2a) and an azide (B9 in FIG. 2a) (Rostovtsev et al. A stepwise huisgen cycloaddition process: copper(I)-catalyzed regioselective "ligation" of azides and terminal alkynes. *Angew. Chem. Int. Ed.* 41, 2596-9 (2002); incorporated herein by reference). Two pmol total of pool A members were combined with 2 pmol total of pool B members (12 fmol of material encoding each possible substrate combination) in the presence of 500 µM Cu(I) in a total volume of 12 µL. After 10 min at 25° C., the salts were removed and disulfide linkages were cleaved with 0.1 M tris-carboxyethylphosphine hydrochloride (TCEP). A control experiment lacking Cu(I) but identical in all other respects was also performed.

Sequences encoding bond-forming substrate pairs were captured with streptavidin-linked magnetic particles and amplified by PCR using a Cy3-labeled DNA primer. For comparison, an aliquot of the pool A sequences before selection was amplified by PCR using a Cy5-labeled primer. The Cy3- and Cy5-labeled PCR products were combined and hybridized to a DNA microarray containing all 168 possible reaction-encoding sequences. The ratios of Cy3 (green) to Cy5 (red) fluorescence for all array locations were calculated and rank ordered, and spots with green:red fluorescence ratios significantly higher than the majority of spots (in the experiments below, ratios>1.5) were considered positives. A prequantitated internal standard (bottom right corner of the array images in FIG. 2b) corresponding to a moderate level of reactivity was used as a positive control and as a reference for comparing different arrays.

For the experiment performed in the presence of Cu(I), the array spot corresponding to the combination of the alkyne (A5) and the azide (B9) was the sole spot that had a significant green:red fluorescence ratio (A5+B9=8.5, standard=2.8; see FIG. 2b and Supplementary Data). In contrast, the experiment performed in the absence of any added metal yielded no green array spots other than the standard (FIG. 2b). These results demonstrate that the above method can detect a single bond-forming substrate combination from a complex mixture of 168 combinations, and confirms the high chemoselectivity characteristic of the Sharpless-modified Huisgen cycloaddition reaction (Wang, Q. et al. Bioconjugation by copper(I)-catalyzed azide-alkyne [3+2] cycloaddition. *J. Am. Chem. Soc.* 125, 3192-3 (2003); incorporated herein by reference).

Cu(I) damages DNA by promoting radical-mediated processes (Burrows et al. Oxidative nucleobase modifications leading to strand scission. *Chem. Rev.* 98, 1109-1152 (1998); incorporated herein by reference). Indeed, we observed 48% degradation of a DNA oligonucleotide exposed for 10 minutes to the Cu(I)-containing conditions (Supplementary Data in Experimentals below). The successful detection of the alkyne-azide cycloaddition under conditions that degrade DNA demonstrates that reaction conditions do not need to be fully DNA compatible, as the extreme sensitivity of PCR amplification (Kramer et al. *Current Protocols in Molecular Biology* (ed. Ausubel, F. M.) (Wiley, 1999); incorporated herein by reference) enables bond formation to be revealed even if a significant fraction of the total DNA in an experiment is destroyed.

To further validate this reaction discovery system, we performed a selection for bond formation after exposure to organic reagents (1-[3-(dimethylamino)propyl]-3-ethylcarbodiimide hydrochloride (EDC) and N-hydroxysuccinimide (NHS) at pH 6.0) known to promote coupling of amines with carboxylic acids (Bailey et al. in *Comprehensive Organic Functional Group Transformations* (eds. Katritzky, A. R., Meth-Cohn, O. & Rees, C. W.) 257-307 (1997); incorporated herein by reference). Microarray analysis revealed one positive; this spot indeed corresponds to the combination of the carboxylic acid from pool A (A10) and the amine from pool B (B12) (A10+B12=15.6, standard=6.9; see FIG. 2b and Supplementary Data).

After successfully 'rediscovering' known bond-forming reactions, we examined the reactivity of a simple Pd(II) salt. Inorganic Pd salts and complexes involving Pd are known to mediate diverse coupling reactions (Tsuji, J. *Palladium Reagents and Catalysts* (Wiley, N.Y., 1995); incorporated herein by reference), suggesting that Pd can activate a variety of organic functional groups. Selection for bond formation in the presence of 500 µM $Na_2PdCl_4$ for 1 h at 37° C. resulted in five strong positives (A7+B3, A5+B3, A4+B8, A5+B5, A5 homocoupling) with significant green:red fluorescence ratios (3.6 to 2.6; standard=2.9). In addition, we observed five weaker positives (A9+B3, A8+B3, A8+B8, A5+B8, A5+B9) with lower, but possibly significant green:red fluorescence ratios ranging from 1.9 to 1.6 (FIG. 2b and Supplementary Data). One positive representing the combination of aryl iodide (A7) and acrylamide (B3) is consistent with the well-known Heck reaction (Heck, R. F. Palladium-catalyzed vinylation of organic halides. *Org. React.* 27, 345 (1982); Li, C.-J. & Chan, T.-H. *Organic Reactions in Aqueous Media* (John Wiley & Sons, Inc., 1997); each of which is incorporated herein by reference) (assuming formation of some Pd(0) under the reaction conditions). Other positives could be rationalized with mechanistic steps precedented in known Pd-mediated chemistries. For example, the spot indicating bond formation between an olefin (A4) and an aryl boronic acid (B8) is consistent with transmetalation of Pd(II) by the aryl boronic acid (Miyaura, N. & Suzuki, A. Palladium-catalyzed cross-coupling reactions of organoboron compounds. *Chem. Rev.* 95, 2457-2483 (1995); incorporated herein by reference) followed by insertion of an olefin into the Pd-aryl bond and subsequent 13-hydride elimination (Crabtree, R. H. *The Organometallic Chemistry of the Transition Metals* (John Wiley & Sons, Inc., 2001); incorporated herein by reference).

To determine if these array results reflect genuine bond-forming events, we examined the putative reactions corresponding to the above ten spots in separate DNA-templated reactions. Denaturing PAGE analysis indicated that all five strong positives and three of the five weak positives correspond to authentic DNA-templated reactions, while two weak positives (A9+B3 and A5+B9) showed little or no product formation (FIG. 3 and Supplementary Data). We observed no product formation in control reactions in which $Na_2PdCl_4$ was omitted, or in which either of the reactive substrates was replaced with an unreactive alkane group. These findings are consistent with the detection of Pd-dependent reactions that couple substrate groups and do not couple the functionality present in DNA.

We further characterized the PAGE-validated Pd-mediated DNA-templated reactions using MALDI-TOF mass spectroscopy (FIG. 3). The observed product masses are consistent with covalent bond formation. We suggest possible structures consistent with the observed masses for each of the reaction products, but note that other products or mixtures of products are also consistent with the data. Together with the PAGE analysis, these results demonstrate that this reaction discovery system reliably and efficiently reveals bond-forming events even under conditions that cause multiple combinations of substrates to react. Increasing the stringency of the reaction conditions by decreasing the temperature to 25° C. and quenching the reaction after 20 min reduced the number of strong positives to four (A5+B5, A5+B3, A4+B8, A5 homocoupling; green:red fluorescence ratios=3.7 to 2.7; standard=3.5) and the number of weak positives to two (A5+B8 and A5+B9; fluorescence ratios=1.9 and 1.7; see FIG. 2b and Supplementary Data). Consistent with these results, the five authentic bond-forming reactions among this set (all four strong positives and weak positive A5+B8) showed substantial product formation by PAGE analysis when performed under the 25° C. conditions, while the three additional reactions that are listed in FIG. 3 but do not appear as positives in the 25° C. experiment (A8+B8, A8+B3, A7+B3) showed significantly weaker product formation (FIG. 3). Varying the stringency of the reaction conditions prior to selection can therefore efficiently distinguish substrate combinations based on their level of reactivity.

Figure 4:
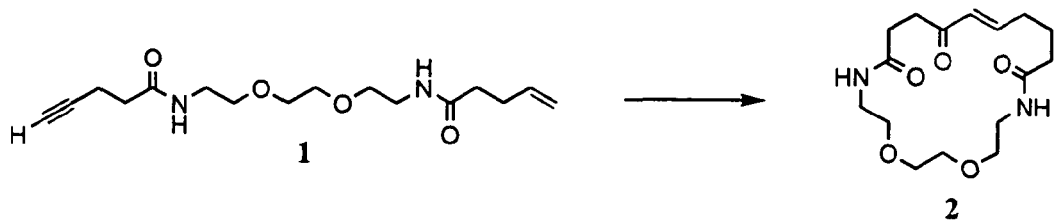
FIG. 4 shows the characterization of a new alkyne-alkene macrocyclization reaction in a non-DNA-templated format. The macrocyclic enone product (2) was characterized by $^1$H-NMR, $^{13}$C-NMR, COSY, UV-VIS spectrometry, and high-resolution mass electrospray (Supplementary Information). We speculate that product formation proceeds through: (i) soft deprotonation of the alkyne to form a Pd(II)-alkynyl intermediate; (ii) insertion of the alkene into the Pd-alkyne bond; (iii) β-hydride elimination to form a conjugated enyne; (iv) Pd(II)-catalyzed hydration of the alkyne to form an enol π-allyl Pd complex; (v) enol tautomerization and π-allyl Pd protonation to generate the trans-enone.)

The above results suggested that the Pd(II)-mediated carbon-carbon bond formation between a simple terminal alkyne and terminal alkene (A5+B5) proceeds efficiently to generate a possible enone product (FIG. 2b and FIG. 3), prompting an in-depth investigation of this reaction. We synthesized a small-molecule substrate (1) to study a non-DNA-templated, intramolecular version of this alkyne-alkene coupling reaction on a multi-milligram scale (FIG. 4). Addition of 1 to one equivalent of Pd(II) in 1 M aqueous NaCl over 15 h followed by reverse-phase HPLC purification provided 20-membered macrocyclic trans-enone 2 as a single olefin stereoisomer in 86% isolated yield (FIG. 4, entry a). The structure of 2 was confirmed by $^1$H-NMR, $^{13}$C-NMR, homonuclear COSY, and high-resolution mass spectroscopy (Supplementary Data). To our knowledge, this is the first example of macrocyclic enone formation from a simple alkyne-alkene precursor. The finding also demonstrates that a reaction discovered using a selection for DNA-templated covalent bond formation can operate in a non-DNA templated format on a much larger ($10^9$-fold) scale.

Since the formation of an enone from an alkyne and an alkene represents an oxidative coupling, we hypothesized that the reaction could be performed with catalytic quantities of Pd by introducing an oxidant such as $CuCl_2$+air to reoxidize Pd(0) to Pd(II) (Smidt, J. et al. Olefinoxydation mit palladiumchlorid-katalysatoren. Angew. Chem. 74, 93-102 (1962); incorporated herein by reference). Indeed, addition of 1 to 5 mol % Pd and 1 equivalent of $CuCl_2$ over 2 h in water at 25° C. provided enone 2 as the sole observed product in 90% isolated yield (FIG. 4, entry b). Significantly, this reaction maintains its high efficiency in organic solvent using 9:1 THF:water (FIG. 4, entry c). Product was formed in similar yields, though at a slower rate, using 1 atm $O_2$ instead of $CuCl_2$ to reoxidize Pd(0) (FIG. 4, entry d). Control reactions with $CuCl_2$ or CuCl alone yielded no observed product formation (FIG. 4, entries e and f).

The discovery of this alkyne-alkene coupling reaction suggests the value of searching a large number of substrate combinations for unanticipated reactions. While aqueous Pd(II) has been known for over 40 years to rapidly oxidize alkenes to ketones (Smidt et al. Olefinoxydation mit palladiumchlorid-katalysatoren. Angew. Chem. 74, 93-102 (1962); Smidt et al. Katalytische umsetzungen von olefinen an platinmetall-verbindungen: das consortium-verfahren zur herstellung von acetaldehyd. Angew. Chem. 71, 176-182 (1959); each of which is incorporated herein by reference) which are unreactive towards alkynes under these conditions (FIG. 2b and Supplementary Data), our approach to reaction discovery revealed that carbon-carbon bond formation between alkynes and alkenes can out-compete alkene oxidation. Although other enone-forming coupling reactions such as the Horner-Wadsworth-Emmons reaction (W. S. Wadsworth, J. & Emmons, W. D. Utility of phosphonate carbanions in olefin synthesis. J. Am. Chem. Soc. 83, 1733-8 (1961); incorporated herein by reference) or aldol condensation are known, the mild reaction conditions, simple hydrocarbon starting materials and high efficiency of the transformation discovered here render it an attractive alternative for addressing some macrocyclization problems in organic synthesis. In addition, the compatibility of this reaction with both organic and aqueous solvents may facilitate the synthesis of highly functionalized macrocyclic enones, of which there are numerous known biologically active examples (Staunton, J. & Weissman, K. J. Polyketide biosynthesis: a millennium review. Nat. Prod. Rep. 18, 380-416 (2001); incorporated herein by reference).

Six of the eight observed heterocoupling reactions in FIG. 3 involve a substrate that couples with itself under the reaction conditions (reactions involving either the alkyne or the aryl boronic acid, see Supplementary Data). In a DNA-templated format, heterocoupling without competitive homocoupling is possible because a substrate experiences a heterocoupling partner at a much higher effective concentration than it experiences another identical substrate molecule.

Biological macromolecules have previously been used to address specific problems in chemical reactivity (Kohli et al. Biomimetic synthesis and optimization of cyclic peptide antibiotics. Nature 418, 658-61 (2002); Breslow, Biomimetic chemistry and artificial enzymes: catalysis by design. Acc. Chem. Res. 28, 146-153 (1995); Schultz & Lerner Completing the circle. Nature 418, 485 (2002); each of which is incorporated herein by reference). In contrast, our approach uses the ability of nucleic acids to direct effective molarities and undergo in vitro selection and amplification to reveal bond-forming reactivity in a general manner. Once DNA-linked substrate pools are prepared, a single researcher can evaluate thousands of combinations of substrates and reaction conditions per two-day experiment. This efficiency enables the search for new reactions between simple, accessible, and relatively unreactive functional groups that are desirable substrates for organic synthesis. Our approach currently requires water-soluble catalysts and aqueous reaction conditions, but as shown above some of the discovered reactions will proceed in a non-DNA-templated format in organic solvents. We anticipate that a broad examination of reaction conditions including transition metal complexes, Lewis acids, oxidants or reductants, and organic reagents using this approach will lead to the discovery of additional bond-forming reactions.

Experimentals:

General Experimental Methods

DNA oligonucleotides were synthesized using standard automated solid-phase phosphoramidite coupling methods on a PerSeptive Biosystems Expedite 8909 DNA synthesizer. All reagents and phosphoramidites for DNA synthesis were purchased from Glen Research. Oligonucleotides were purified by reverse-phase High Pressure Liquid Chromatography (HPLC) using a C18 stationary phase and an acetonitrile/100 mM triethyl ammonium acetate (TEAA) gradient and quantitated using UV spectroscopy. Labeled oligonucleotides were purified by HPLC and characterized by MALDI-TOF mass spectroscopy using a hydroxypicolinic acid/ammonium citrate matrix. Observed masses were within 0.075% of expected masses. All $H_2O$ used in the manipulations below was obtained from a Milli-Q purification system.

For purification and characterization of small-molecule products arising from non-DNA-templated reactions, analytical HPLC was performed on an Agilent 1100 Series instrument equipped with a Varian Pursuit C18 reverse-phase semi-preparative column. Preparative HPLC was performed on a Varian ProStar instrument equipped with a Varian Pursuit C18 1.0 gram-scale preparative reverse-phase column. Proton magnetic resonance ($^1$H-NMR), carbon nuclear magnetic resonance ($^{13}$C-NMR), and COSY spectra were obtained using Varian Mercury 400 (400 MHz) and Varian INOVA500

(500 MHz) NMR spectrophotometers at 25° C. Small-molecule products were further analyzed by electrospray mass spectroscopy.

Preparation of Pool A DNA-linked Substrates

Pool A Oligonucleotide Sequence Design

Complete pool A templates contain (from 5' to 3'): a 15-base 5' PCR primer-binding site, a 15-base annealing region complementary to a pool B sequence, an 8-base constant region, a 12-base coding region used to identify the attached substrate, and a 15-base 3' PCR primer binding site (FIG. 5). Each pool A small-molecule substrate is attached to a pool A oligonucleotide through an amide linkage at the 5' end of the oligonucleotide.

Preparation of Component Oligonucleotides for the Modular Assembly of Pool A

Pool A DNA-linked substrates were assembled in a convergent, modular manner using four types of oligonucleotides: "coding", "annealing", "splint", and "substrate-linked" (FIG. 5). The description and preparation of each type are detailed below.

Coding oligonucleotides are 35 bases long and consist of (5' to 3'): a 15-base PCR primer-binding site, a 12-base coding region, an 8-base constant region, and a 3'-modified group (arising from the C7 amino CPG). This 3' modification ensured that only the annealing oligonucleotides (which have natural 3'-OH groups) were substrates for primer extension during pool A assembly (FIG. 5).

Annealing oligonucleotides are 28 bases long and contain (5' to 3'): a 5'-phosphate installed with Chemical Phosphorylating Reagent II, a 5-base portion of the 5'-PCR primer binding site, a unique 15-base annealing region, and an 8-base constant region complementary to the 8-base constant region present in the coding oligonucleotide. The 5'-phosphate group enabled these sequences to undergo a ligation reaction with the 3'-OH of the "substrate-labeled" oligonucleotides during pool A assembly (see below).

Splint oligonucleotides are 25-base sequences consisting of (5' to 3'): 15 bases complementary to an annealing region, 5 bases complementary to the 5' end of the annealing oligonucleotides, and 5 bases complementary to the 3' end of the substrate-linked oligonucleotides.

Substrate-linked oligonucleotides are 10-base sequences containing (5' to 3'): a 5' amino group (installed using the Amino-Modifier 5 phosphoramidite), and 10 bases representing the 5'-end of the 5' PCR primer binding site. This oligonucleotide was labeled with 12 different carboxylic acids (or activated carboxylic acid derivatives) in separate reaction vessels. For a typical labeling reaction, a carboxylic acid was pre-activated as an NHS ester by combining 0.9 M solutions of the carboxylic acid, N-hydroxysuccinimide (NHS), and 1,3-dicyclohexyl carbodiimide (DCC) in a 1:1:1 ratio and letting the reaction proceed at 25° C. for 40 min. The DCU precipitate in these reactions was pelleted by microcentrifugation and the supernatant was used directly in a labeling reaction. For those substrates that were commercially available as activated carboxylic acid derivatives, a 10 mg/mL stock solution in DMF was prepared and added directly to the labeling reaction. A typical labeling reaction consisted of 10 nmol of amino-terminated oligonucleotide in 100 μL of 0.2 M phosphate buffer at pH 8.0, to which 45 μL of the NHS ester solution was added. After 2 h at 25° C., labeling reactions were passed through a Nap-5 sephadex gel-filtration column (Amersham Biosciences) and the labeled oligonucleotide was purified by reverse-phase HPLC. See table below for MALDI characterization of each substrate-linked oligonucleotide used in the assembly of the pool A members.

The carboxylic acids (or carboxylic acid derivatives) used for the preparation of pool A were all obtained from commercial sources as follows: hexanoic acid (A1, Aldrich), cyclopropylacetic acid (A2, Oakwood Products), cyclobutanecarboxylic acid (A3, Aldrich), trans-3-hexenoic acid (A4, Aldrich), 6-heptynoic acid (A5, Aldrich), phenylacetic acid (A6, Aldrich), 4-iodobenzoic acid (A7, Aldrich), 3-(2-furyl) propanoic acid (A8, Acros), indole-5-carboxylic acid (A9, Aldrich), succinic anhydride (A10, Aldrich), methyl N-succinimidyl adipate (A11, Pierce), 6-oxoheptanoic acid (A12, Aldrich).

Modular Assembly of Pool A Members

The complete pool A DNA-linked substrates were assembled from the above components by primer extension and ligation (FIG. 5). A one-pot primer extension appended the coding sequence for a pool A member to 13 different annealing oligonucleotides and a subsequent ligation assisted by the splint oligonucleotides linked the pool A substrate encoded by the coding sequence to each of the 13 primer extension products. Primer extensions were performed on a 500 pmol scale (5 μM coding sequence and 5 μM total annealing sequences) in 100 μL at 25° C. for 3 h using Klenow exo⁻(New England Biolabs). In addition to the coding and annealing sequences, 1 nmol of the splint oligonucleotides necessary for the ligation step was added to the primer extension step to minimize the formation of internal secondary structure within the annealing sequences.

Ligations were performed directly following buffer exchange of the primer extension reactions. One nmol of the appropriate 5'-pool A substrate-linked oligonucleotide (two equiv. with respect to the primer extension products, one equiv. with respect to the splint oligonucleotides) was added to the buffer-exchanged reaction and the ligation was performed overnight at 16° C. using T4 DNA ligase. Ligation reactions were precipitated with ethanol and full-length single-stranded pool A DNA-linked substrates were purified by denaturing PAGE. Typically, a 500 pmol-scale assembly of a pool A DNA-linked substrate yielded≧100 pmol of purified full-length templates. The mass spectroscopic analysis of the substrate-linked oligonucleotides used in the assembly of pool A is shown below in Table 1.

TABLE 1

MALDI-TOF characterization of pool A substrate-linked oligonucleotides.

| Substrate | Expected mass of DNA-linked substrate | Observed mass |
| --- | --- | --- |
| hexanoic acid (A1) | 3281.7 | 3281 ± 3 |
| cyclopropylacetic acid (A2) | 3265.6 | 3267 ± 3 |
| cyclobutane carboxylic acid (A3) | 3265.6 | 3267 ± 3 |
| 3-hexenoic acid (A4) | 3279.6 | 3280 ± 3 |
| 6-heptynoic acid (A5) | 3291.6 | 3292 ± 3 |
| phenylacetic acid (A6) | 3301.6 | 3304 ± 3 |
| 4-iodobenzoic acid (A7) | 3413.5 | 3414 ± 3 |
| 3-(2-furyl)propanoic acid (A8) | 3305.6 | 3306 ± 3 |
| indole-5-carboxylic acid (A9) | 3326.6 | 3327 ± 3 |
| succinic acid (A10) | 3283.6 | 3385 ± 3 |
| adipic acid monomethyl ester (A11) | 3325.6 | 3326 ± 3 |
| 6-oxoheptanoic acid (A12) | 3309.6 | 3310 ± 3 |

Preparation of Pool A DNA-linked Substrates for the Detection of Pool B Homocoupling In addition to the 12 pool A members described above (each containing 13 different sequences), 12 individual pool A sequences were prepared, each linked to a different pool B substrate. These DNA-linked substrates were designed to enable detection of homocoupling of any of the pool B substrates. Each of these DNA-linked substrates was prepared in a manner analogous to the preparation of pool A members described above except that only one annealing oligonucleotide and only one splint oligonucleotide were used in the primer-extension and ligation steps. Additionally, all of these DNA-linked substrates were prepared using the same coding oligonucleotide (rather than coding for a substrate, this coding sequence encoded for homocoupling). Mass spectroscopic characterization of the substrate-linked oligonucleotides is provided in Table 2.

TABLE 2

MALDI-TOF characterization of pool A substrate-linked oligonucleotides for the detection of pool B homocoupling.

| Substrate | Expected mass of DNA-linked substrate | Observed mass |
| --- | --- | --- |
| 5-chlorovaleric acid (B1) | 3301.6 | 3303 ± 3 |
| p-formylbenzoic acid (B2) | 3315.6 | 3317 ± 3 |
| acrylic acid (B3) | 3237.6 | 3240 ± 3 |
| 5-oxiranyl pentanoic acid (B4) | 3309.6 | 3313 ± 3 |
| 6-heptenoic acid (B5) | 3293.7 | 3293 ± 3 |
| 3-(4-hydroxy-phenyl) propionic acid (B6) | 3331.6 | 3332 ± 3 |
| 5-methoxycarbonyl-4-oxopentanoic acid (B7) | 3339.6 | 3342 ± 3 |
| 4-(2-carboxyethyl) benzeneboronic acid (B8) | 3515.8 (citric acid adduct) | 3516 ± 3 |
| 4-azidobutyric acid (B9) | 3294.6 | 3296 ± 3 |
| 8-cyano-octanoic acid (B10) | 3334.7 | 3336 ± 3 |
| 6-hydroxycaproic acid (B11) | 3297.6 | 3298 ± 3 |
| unlabeled amine (no carboxylic acid) (B12) | 3183.6 | 3185 ± 3 |

Preparation of Pool B

Pool B DNA-linked substrates are 16 bases in length and contain (5' to 3'): a 15-base annealing region complementary to one of the annealing regions in pool A, a single C, a disulfide linker, a biotin group, and an amide-linked substrate (FIG. 5). The modified groups were introduced using the 3' PT Amino-Modifier C6 CPG, the biotin phosphoramidite, and the thiol modifier C6 S—S. The 3' amine-terminated oligonucleotides were labeled with the appropriate activated carboxylic acid using the protocol described in the preparation of pool A. The purified labeled oligonucleotides were characterized by mass spectroscopy as is shown below. In all, 24 DNA-linked substrates were prepared and characterized in this manner comprising 12 DNA-linked pool B substrates and 12 additional DNA-linked substrates for detection of homocoupling of any of the pool A substrates.

The following carboxylic acids or carboxylic acid derivatives used in the preparation of pool B were available from commercial sources: 5-chlorovaleric acid (Aldrich, B1), p-formylbenzoic acid N-hydroxysuccinimide ester (Aldrich, B2), acrylic acid (Aldrich, B3), 6-heptenoic acid (Aldrich, B5), 3-(4-hydroxy-phenyl)propionic acid N-hydroxysuccinimide ester (Aldrich, B6), 4-(2-carboxyethyl)benzeneboronic acid (Lancaster, B8), and 6-hydroxycaproic acid (Aldrich, B11). 5-methoxycarbonyl-4-oxopentanoic acid (B7) was prepared according to a literature procedure (Oku, A., Numata, M. *J. Org. Chem.* 65 1899-1906 (2000)). 4-azidobutyric acid (B9) was prepared according to a literature procedure (Kusumoto, S., Sakurai, K., Shiba, T. *Bull. Chem. Soc. Jpn.* 59, 1296-1298 (1986)). 5-oxiranyl pentanoic acid (B4) was prepared from 6-heptenoic acid using the epoxidation procedure described in Corey, P. F., Ward, F. E. *J. Org. Chem.* 51, 1925-1926 (1986). $^1$H NMR (CDCl$_3$): δ=1.50-1.61 ppm (m, 4H), 1.67-1.74 (m, 2H), 2.38 (t, 2H), 2.48 (dd, 1H), 2.76 (t, 1H), 2.92 (m, 1H). HRMS: calculated=162.1130 (NH$_4^+$); observed=162.1125. $^{13}$C NMR (CDCl$_3$): δ=24.63, 25.66, 32.28, 34.06, 47.29, 52.34, 179.66.

Preparation of 8-Cyano-octanoic Acid (Substrate B10).

The preparation of the cyano-carboxylic acid representing substrate B10 was adapted from a procedure for the preparation of 4-(2-cyanoethyl)benzoic acid (Delia, T. J., Baumann, M., Bunker, A. *Heterocycles,* 35, 1397-1410 (1993)). To 501 mg (2.25 mmol) of 8-bromooctanoic acid in 7.0 mL of methanol was added 520 mg NaCN (10.6 mmol) in 2.0 mL H$_2$O. The solution was heated at reflux for 2.5 h. After cooling to 25° C., the solution was acidified to pH~1.5 with concentrated HCl (caution: HCN gas evolves with the addition of HCl) and diluted with 40 mL EtOAc. The resulting suspension was washed twice with 15 mL H$_2$O. The organic layer was dried by filtration through MgSO$_4$, and the solvent was removed in vacuo to afford 282 mg (74%) of a light brown oil. The $^1$H NMR spectrum agreed with previously reported data in Cotarca et al. *Synthesis* 1997, 328-332.

Mass spectroscopic characterization of pool B members are shown in Tables 3 and 4.

TABLE 3

MALDI-TOF characterization of pool B members.

| Substrate | Expected mass of DNA-linked substrate | Observed mass |
| --- | --- | --- |
| 5-chlorovaleric acid (B1) | 5922.3 | 5922 ± 5 |
| 4-formylbenzoic acid (B2) | 5896.2 | 5895 ± 5 |
| acrylic acid (B3) | 5778.2 | 5778 ± 5 |
| 5-oxiranyl pentanoic acid (B4) | 5952.3 | 5952 ± 5 |
| 6-heptenoic acid (B5) | 5874.3 | 5874 ± 5 |
| 3-(4-hydroxy-phenyl) propionic acid (B6) | 5823.2 | 5823 ± 5 |
| 5-methoxycarbonyl-4-oxopentanoic acid (B7) | 5960.3 | 5960 ± 5 |
| 4-(2-carboxyethyl) benzeneboronic acid (B8) | 6145.3 (citric acid adduct) | 6145 ± 5 |
| 4-azidobutyric acid (B9) | 5755.2 | 5754 ± 5 |
| 8-cyano-octanoic acid (B10) | 5906.3 | 5907 ± 5 |
| 6-hydroxycaproic acid (B11) | 5869.3 | 5869 ± 5 |
| unlabeled amine (no RCOOH) (B12) | 5775.3 | 5775 ± 5 |

TABLE 4

MALDI-TOF characterization of pool B members for the detection of pool A homocoupling

| Hexanoic acid (A1) | 5835.3 | 5835 ± 5 |
| --- | --- | --- |
| Cyclopropylacetic acid (A2) | 5855.3 | 5854 ± 5 |
| Cyclobutanecarboxylic acid (A3) | 5917.3 | 5917 ± 5 |
| 3-hexenoic acid (A4) | 5891.3 | 5891 ± 5 |
| 6-heptynoic acid (A5) | 5845.2 | 5843 ± 5 |
| Phenylacetic acid (A6) | 5873.3 | 5873 ± 5 |
| 4-iodobenzoic acid (A7) | 6003.2 | 6003 ± 5 |
| 3-(2-furyl)propionic acid (A8) | 5877.3 | 5877 ± 5 |
| Indole-5-carboxylic acid (A9) | 5876.3 | 5875 ± 5 |
| Succinic acid (A10) | 5815.2 | 5814 ± 5 |
| Adipic acid monomethylester (A11) | 5906.3 | 5906 ± 5 |
| 6-oxoheptanoic acid (A12) | 5819.3 | 5818 ± 5 |

Preparation of DNA Microarrays

Commercial 5'-amino-modified oligonucleotides (Illumina) were printed on aldehyde-silane glass slides (Schott-Nexterion) using a robotic microarrayer (GeneMachines).

Stock solutions for printing were 20 µM in 3×SSC buffer. Fifteen copies of the microarray were printed on each slide, in 5 columns of 3 copies each. This enabled each analyte sample to be hybridized to three different microarrays per experiment. In all cases, the three replicate microarrays per experiment gave virtually indistinguishable signals. Printed oligonucleotides were immobilized and unreacted aldehydes on the slides were blocked according to the manufacturer's protocol with one 15 s concentrated $NH_4OH$ wash followed by a 1 min $H_2O$ wash added to the end of the blocking procedure. After blocking, slides were stored in a dessicator covered with aluminum foil and used within two weeks.

Each printed oligonucleotide representing a unique combination of substrates was a 35-mer consisting of (5' to 3') one of the 15-base annealing regions, an 8-base constant region, and one of the 12-base coding regions from the pool A sequences. The $169^{th}$ oligonucleotide used to detect the internal standard (see Selections for Bond Formation) shared only the constant region with any of the other 168 sequences and was printed in the lower right corner of each array.

Selections for Bond-Formation

Internal Standard Oligonucleotide:

To compare fluorescence intensity ratios between arrays, a biotinylated oligonucleotide was included in each selection at an amount equal to $\frac{1}{10}^{th}$ of the amount of an individual pool A sequence encoding a unique substrate combination. This oligonucleotide served as an internal standard representing~10% DNA-templated reactivity in a selection. The reference oligonucleotide was synthesized with a 5' biotin group using the 5' Biotin Phosphoramidite and purified by Oligonucleotide Purification Cartridge (OPC, Applied Biosystems, Inc.)

Universal Clamp Oligonucleotide

To minimize secondary structure in the pool A oligonucleotides, a "universal clamp" oligonucleotide was included in each selection for bond formation. This oligonucleotide consisted of (5' to 3') 15 bases complementary to the 3' primer binding site of the pool A sequences and 8 bases complementary to the constant region of the pool A sequences.

Selection Components

A typical selection for bond-formation used five components: pool A, pool B, a "universal clamp", the biotinylated internal standard, and the metal complex or reagents being tested. For selections, stock solutions were prepared for each pool. The stock solution for pool A was 1 µM in total DNA and contained equal amounts of each of the 168 different oligonucleotides (encoding the 144 heterocoupling and 24 homocoupling substrate combinations) in addition to $\frac{1}{10}$ of an equivalent of the biotinylated internal standard oligonucleotide. The stock solution for pool B was 2 µM in total DNA and contained equal amounts of each of the 12 pool B oligonucleotides and $\frac{1}{12}$ of one equivalent of each of the "self-A" homocoupling-encoding oligonucleotides.

Reaction Discovery Experiments and Selection Procedure

Each reaction discovery experiment was performed in 12 µL total solution containing 12 fmol of material representing each unique substrate combination. Two pmol of total pool A material, 2 pmol of total pool B material, 8 pmol of the universal clamp, and 1.2 fmol of the biotinylated internal standard were combined in buffer and allowed to hybridize at 25° C. for 30 min. Reactions were initiated by adding 1 µL of a solution containing the metal or non-DNA-linked reagents. The detailed conditions for each experiment shown in FIG. 2b are as follows:

No metal: 50 mM MOPS, 0.5 M NaCl, pH 7.0, 37° C., 1 h.

Cu(I): 500 µM $CuSO_4$, 500 µM sodium ascorbate, 50 mM MOPS, 0.1 M $Na_2SO_4$, pH 7.0, 25° C., 10 min.

EDC+sNHS: 20 mM EDC, 15 mM sNHS, 50 mM MES, 0.5 M NaCl, pH 6.0, 25° C., 1 h.

Pd(II), 37° C.: 500 µM $Na_2PdCl_4$, 50 mM MOPS, 0.5 M NaCl, pH 7.0, 1 h.

Pd(II), 25° C.: 500 µM $Na_2PdCl_4$, 50 mM MOPS, 0.5 M NaCl, pH 7.0, 20 min.

After the reaction times indicated above, the solution was diluted with 20 µL of $H_2O$ and passed through a gel filtration microcentrifuge column (Princeton Separations) to remove small-molecule reactants. To the eluant was added 150 µL of a 0.1 M aqueous solution of tris(2-carboxyethyl)phosphine hydrochloride in 1.0 M sodium phosphate, pH 8.0 to effect disulfide cleavage. After 1 h at 25° C., this solution was added to a 20 pmol binding-capacity aliquot of streptavidin-linked magnetic particles (Roche Biosciences) suspended in 300 µL of 0.1 M NaCl, 10 mM Tris, 1 mM EDTA, pH 7.5 ("loading buffer"). The supernatant was removed after 15 min. The particles were rinsed once with 200 µL $H_2O$, and once with 200 µL 1 M NaCl, 10 mM Tris, 1 mM EDTA, pH 7.5 ("washing buffer"). The particles were then resuspended in 20 µL of 95% formamide-5% 10 mM EDTA and incubated at 65° C. for 10 min. Fifteen µL of this eluant was diluted with 60 µL $H_2O$ and added to a fresh aliquot of streptavidin particles suspended in 350 µL of loading buffer. After 15 min, the supernatant was removed and the particles were rinsed with $H_2O$ and washing buffer as above. The particles were resuspended in 15 µL of 95% formamide-5% 10 mM EDTA and incubated at 90° C. for 10 min. Ten µL of this eluant was diluted with 35 µL $H_2O$ and passed through a gel filtration spin-column (Princeton Separations). This solution was used directly in PCR reactions for microarray analysis.

Microarray Analysis of Selections

Preparation of PCR Primers

Primer 1 was synthesized using standard automated methods and purified using an OPC column to avoid trace contaminants from HPLC purification that could be amplified in a PCR reaction. Primer 2 was synthesized with the C6 Amino-dT phosphoramidite in place of the dT monomer and also purified by OPC. (See the DNA Oligonucleotide Sequences section for the primer sequences). A solution of 0.5 µmol primer 2 in 200 µL of 0.1 M sodium carbonate pH 9.3 was added to a Cy-3 Mono-Reactive Dye Pack (Amersham Biosciences) and the solution was agitated in the dark at 25° C. for 1 h before being passed through a gel filtration spin-column and a Nap-5 gel filtration column. The Nap-5 eluant was quantitated by UV and stored at −80° C. until it was used in a PCR reaction. A 0.5 µmol aliquot of primer 2 was labeled with Cy-5 using an identical procedure with the Cy-5 Mono-Reactive Dye Pack.

Blocking Oligonucleotides

Twenty-three-base oligonucleotides complementary to each annealing region +constant region and 20-base oligonucleotides complementary to each constant region +coding region present on the array were purchased from Illumina. These oligonucleotides were included in the hybridization solution to maximize annealing fidelity.

PCR Amplification of Pre- and Post-Selection Sequences and Microarray Analysis

Ten µL aliquots of selected sequences (see Selections for Bond Formation) were added to a 250 µL PCR reaction containing 2.5 mM $MgCl_2$, 0.2 mM dNTPs, 40 nM primer 1, and 400 nM primer 2 labeled with Cy-3. The sequences were amplified with 35 cycles of 95° C. for 30 s, 55° C. for 30 s, and 72° C. for 20 s. Forty fmol of an equimolar mixture of the 169 pool A sequences (including the internal standard sequence) was amplified by PCR under identical conditions using primer 2 labeled with Cy-5. The PCR reactions were extracted with phenol-chloroform and precipitated with EtOH. A pre-selection pellet (Cy-5-labeled) and post-selection pellet (Cy-3-labeled) were resuspended together in 24 μL of 20 mM HEPES pH 7.5, 1×SSC containing 10 μg BSA and 10 μM blocking oligonucleotides. The solution was filtered using a 0.45 μM microcentrifuge filter (Millipore). Six μL of formamide and 0.45 μL of 10% SDS were added to the filtrate and the solution was heated to 100° C. for 2 min. After cooling to room temperature, this solution was hybridized at 65° C. for 12 h to the DNA microarray described above. After hybridization, the slides were washed with 0.025% SDS, 0.6×SSC (5 min) and 0.05×SSC (5 min) and scanned immediately using an Axon GenePix 4000B scanner (Axon Instruments).

DNA Oligonucleotide Sequences and Linker Structures

Pool A oligonucleotide sequence:

```
5'-CGTTGATATCCGCAGXXXXXXXXXXXXXXXCACA  (SEQ ID NO: 1)
CACCYYYYYYYYYYYYGCCAGCTGCTAGCTT-3'
``` where XXXXXXXXXXXXXXX (the annealing region) is one of the following:

| | | |
|---|---|---|
| AACTTCCTCTCGGGA | (SEQ ID NO: 2) | |
| ACGCGATGTTTCGAC | (SEQ ID NO: 3) | |
| AGCGTTATGGTCCGA | (SEQ ID NO: 4) | |
| ACATGAGCCCCACTA | (SEQ ID NO: 5) | |
| CCACTGTTACTAGGG | (SEQ ID NO: 6) | |
| CGTGCTTGAGGAGAA | (SEQ ID NO: 7) | |
| AGGCCTCTTTAGACC | (SEQ ID NO: 8) | |
| CTTAGTTTCGCGCAC | (SEQ ID NO: 9) | |
| GAGGGTGATGCATGT | (SEQ ID NO: 10) | |
| GCTGGACTAGCTACA | (SEQ ID NO: 11) | |
| TAGACACGCATGTGC | (SEQ ID NO: 12) | |
| TCGGACTTTGATGGC | (SEQ ID NO: 13) | |
| ACCGAAGGGCAATAC | (SEQ ID NO: 14) | |
| GTCAGCCCTTGGTAT | (SEQ ID NO: 15) | |
| CACCTACCGGTAATC | (SEQ ID NO: 16) | |
| CAGTCCGGTACCTAA | (SEQ ID NO: 17) | |
| CCTGAGAAAGAACCG | (SEQ ID NO: 18) | |
| TTGATGACCAGGCCA | (SEQ ID NO: 19) | |
| TGCGCAACTGGTCTT | (SEQ ID NO: 20) | |
| TGGCAAATCCAGCGT | (SEQ ID NO: 21) | |
| GACCTTGGCGTTTAG | (SEQ ID NO: 22) | |
| TCCAGGGGATGCATA | (SEQ ID NO: 23) | |
| GCACGTACATTGCTG | (SEQ ID NO: 24) | |
| GGTGTATACGTGGCT | (SEQ ID NO: 25) | | and YYYYYYYYYYYY (the coding region) is one of the following:

| | | |
|---|---|---|
| AAGCTGATCACG | (A1) | (SEQ ID NO: 26) |
| TAGTGCCGTTGA | (A2) | (SEQ ID NO: 27) |
| ACCATATCCCCT | (A3) | (SEQ ID NO: 28) |
| ACGTATAGCGGT | (A4) | (SEQ ID NO: 29) |
| AGAAAGTGTGCG | (A5) | (SEQ ID NO: 30) |
| ATAGTTGGCTCC | (A6) | (SEQ ID NO: 31) |
| ATCTGGAACCTC | (A7) | (SEQ ID NO: 32) |
| ATTCAACCGTCG | (A8) | (SEQ ID NO: 33) |
| CACCGAAGTAAC | (A9) | (SEQ ID NO: 34) |
| TTGGAGCCTGAT | (A10) | (SEQ ID NO: 35) |
| CCCTCCTTATCA | (A11) | (SEQ ID NO: 36) |
| TGTCGGGACAAT | (A12) | (SEQ ID NO: 37) |
| TGCTAATGACGC | (SELF-B) | (SEQ ID NO: 38) |

Annealing and coding sequences were generated by computer algorithms to minimize undesired reactivity arising from the mismatched hybridization of a pool B member with a non-complementary pool A member. The overall GC/AT ratio of these sequences was kept constant to minimize differences in melting temperatures between different annealing and coding sequences.

Internal standard oligonucleotide sequence:

```
5'CGTTGATATCCGCAGGTGCATTAGCACGCACACA (SEQ ID NO: 39)
CACCTCTAACACAGCCGCCAGCTGCTAGCTT-3'
```

Pool B oligonucleotide sequences are as follows:

| | | |
|---|---|---|
| TCCCGAGAGGAAGTTC | (B1) | (SEQ ID NO: 40) |
| GTCGAAACATCGCGTC | (B2) | (SEQ ID NO: 41) |
| TCGGACCATAACGCTC | (B3) | (SEQ ID NO: 42) |
| TAGTGGGGCTCATGTC | (B4) | (SEQ ID NO: 43) |
| CCCTAGTAACAGTGGC | (B5) | (SEQ ID NO: 44) |
| TTCTCCTCAAGCACGC | (B6) | (SEQ ID NO: 45) |
| GGTCTAAAGAGGCCTC | (B7) | (SEQ ID NO: 46) |

```
                        -continued
GTGCGCGAAACTAAGC    (B8)        (SEQ ID NO: 47)

ACATGCATCACCCTCC    (B9)        (SEQ ID NO: 48)

TGTAGCTAGTCCAGC     (B10)       (SEQ ID NO: 49)

GCACATGCGTGTCTAC    (B11)       (SEQ ID NO: 50)

GCCATCAAAGTCCGAC    (B12)       (SEQ ID NO: 51)

GTATTGCCCTTCGGTC    (SELF A1)   (SEQ ID NO: 52)

ATACCAAGGGCTGACC    (SELF A2)   (SEQ ID NO: 53)

GATTACCGGTAGGTGC    (SELF A3)   (SEQ ID NO: 54)

TTAGGTACCGGACTGC    (SELF A4)   (SEQ ID NO: 55)

CGGTTCTTTCTCAGGC    (SELF A5)   (SEQ ID NO: 56)

TGGCCTGGTCATCAAC    (SELF A6)   (SEQ ID NO: 57)

AAGACCAGTTGCGCAC    (SELF A7)   (SEQ ID NO: 58)

ACGCTGGATTTGCCAC    (SELF A8)   (SEQ ID NO: 59)

CTAAACGCCAAGGTCC    (SELF A9)   (SEQ ID NO: 60)

TATGCATCCCCTGGAC    (SELF A10)  (SEQ ID NO: 61)

CAGCAATGTACGTGCC    (SELF A11)  (SEQ ID NO: 62)

AGCCACGTATACACCC    (SELF A12)  (SEQ ID NO: 63)
```

Sequences used in DNA-templated characterization of array positives:

```
30-base oligonucleotide:
5'- CGTTGATATCCGCAGACGCGATGTTTCGAC    (SEQ ID NO: 64)

16-base oligonucleotide:
5'- GTCGAAACATCGCGTC                  (SEQ ID NO: 65)
```

Sequences used in MALDI-TOF analysis of DNA-templated reactions:

```
20-base oligonucleotide:
5'- CATTACCATGTACATACCAG              (SEQ ID NO: 66)

15-base oligonucleotide:
5'- CTGGTATGTACATGG                   (SEQ ID NO: 67)
```

Structure of a pool A oligonucleotide before labeling with a pool A substrate acid:

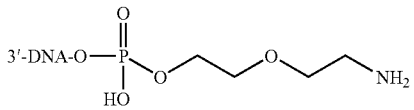

Structure of a pool B oligonucleotide before labeling with a pool B substrate acid:

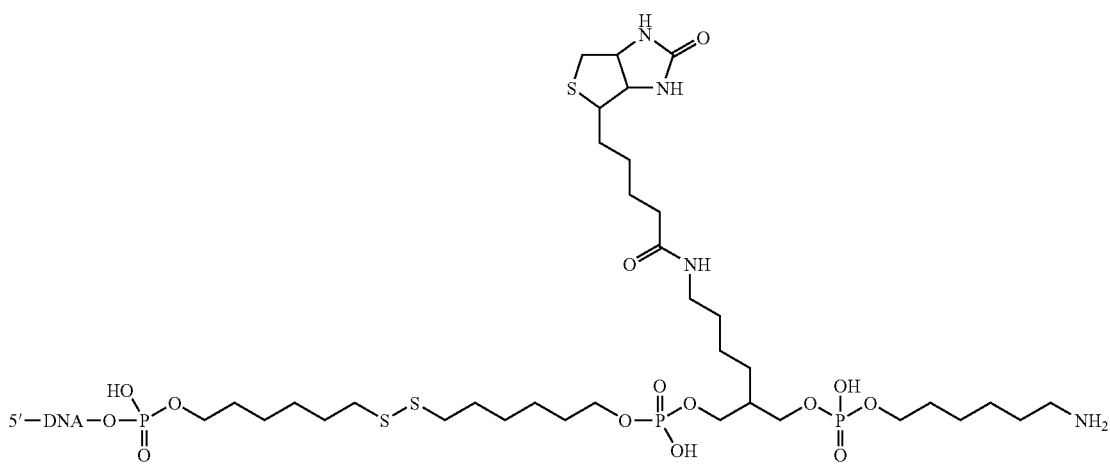

Structure of an unlabeled 16-base oligonucleotide used in the DNA-templated characterization of array positives:

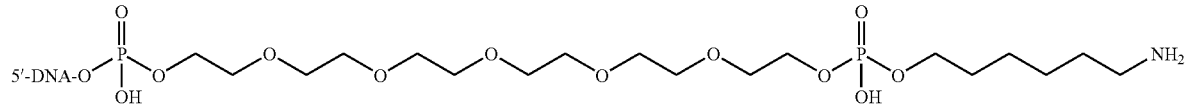

Structure of an unlabeled 15-base oligonucleotide with a cleavable sulfone linker used in the MALDI-TOF characterization of DNA-templated reactions:

substrate. Both oligonucleotides were labeled with appropriate substrates as described in the preparation of the substrate-linked oligonucleotides in pool A. Labeled oligonucleotides were characterized by MALDI-TOF mass spectroscopy (Table 5).

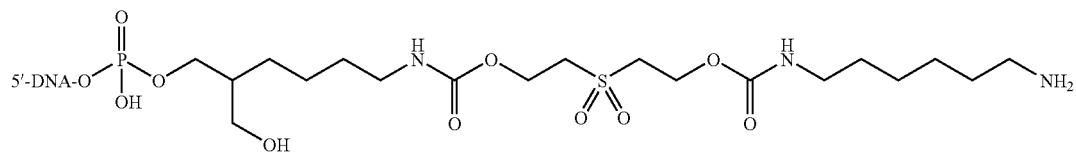

Supplementary Data

Quantitative Microarray Data

The ratio of median green:red fluorescence intensities of the spots on the arrays were calculated using the GenePix Pro 5.0 software. The values for the spots with the highest green:red ratios of median fluorescence in each of the arrays in FIG. 2B are as follows:

Cu(I): A5+B9=8.5; standard=2.8

EDC+sNHS: standard=15.6; A10+B12=6.9

Pd(II), 37° C.: A7+B3=3.6; A5+B3=3.5; A4+B8=3.0; standard=2.9; A5+B5=2.7; A5+B13=2.6; A9+B3=1.9; A8+B8=1.8; A8+B3=1.8; A5+B8=1.6; A5+B9=1.6

Pd(II), 25° C.: A5+B5=3.7; standard=3.5; A5+B3=3.1; A4+B8=2.8; A5+B13=2.7; A5+B8=1.9; A5+B9=1.7

Characterization of Putative Reactions in a DNA-Templated Format

Reactions corresponding to array positives from the Pd(II) selections were performed in a DNA-templated format on a 25 pmol scale and analyzed by denaturing PAGE. Two oligonucleotides were used for these experiments: a 30-base oligonucleotide labeled with a substrate at the 5' end and a 16-base oligonucleotide (complementary to a region of the 30-base oligonucleotide) labeled with a substrate at the 3' end. The 30-base oligonucleotide was synthesized with a 5' amine using the 5'-Amino-Modifier 5 phosphoramidite. The 16-base oligonucleotide was synthesized with a 3' amine using the 3'-PT Amino-Modifier C6 CPG and the Spacer 18 phosphoramidite (see Supplementary Methods for the complete structure). The Spacer 18 phosphoramidite enabled the number of bonds between the substrate and the 3' base of the 16-base oligonucleotide to match the number of bonds between the substrate and the 3' base in a pool B DNA-linked

TABLE 5

MALDI-TOF characterization of DNA-linked substrates for evaluating array positives in a DNA-templated format.

| Substrate | Expected mass of labeled 30-base oligonucleotide | Observed mass |
|---|---|---|
| 3-hexenoic acid (A4) | 9456.6 | 9457 ± 9 |
| 6-heptynoic acid (A5) | 9468.6 | 9468 ± 9 |
| 4-iodobenzoic acid (A7) | 9590.5 | 9591 ± 9 |
| 3-(2-furyl)propionic acid (A8) | 9482.6 | 9481 ± 9 |
| indole-5-carboxylic acid (A9) | 9503.6 | 9502 ± 9 |
| hexanoic acid (negative control) | 9458.7 | 9457 ± 9 |

| Substrate | Expected mass of labeled 16-base oligonucleotide | Observed mass |
|---|---|---|
| acrylic acid (B3) | 5441.05 | 5441 ± 5 |
| 6-heptenoic acid (B5) | 5497.12 | 5497 ± 5 |
| 4-(2-carboxyethyl)benzeneboronic acid (B8) | 5719.11 (citric acid adduct) | 5717 ± 5 |
| 6-heptynoic acid (A5) | 5495.10 | 5494 ± 5 |
| hexanoic acid (negative control) | 5485.10 | 5484 ± 5 |

To perform a DNA-templated reaction, 25 pmol of substrate-linked 30-mer was combined with 37.5 pmol of substrate-linked 16-mer in 360 µL of 0.1 M MOPS, 1 M NaCl, pH 7.0 and allowed to hybridize for at least 20 min. Reactions were initiated by adding 40 µL of a 5 mM solution of $Na_2PdCl_4$ in $H_2O$ and allowed to react for either 20 min at 25° C. or 1 h at 37° C. before the Pd was quenched with 4 µL of 2 M β-mercaptoethanol and the reactions were EtOH precipitated. Ten pmol aliquots of the reactions were electrophoresed on denaturing polyacrylamide gels and the efficiencies of the reactions were determined by quantitation of ethidium bromide staining. Control reactions in which Pd was omitted showed no product formation. Control reactions with Pd in which one of the substrates was replaced with an alkane also showed no product formation, although occasionally we observed faint diffuse higher molecular weight bands that we attribute to Pd-complexed species. In the case of the reaction discovery selections, cleavage of the disulfide linker prevents Pd complexation from generating false positives. Reaction yields were quantitated by UV visualization of stained gels and densitometry of product and starting material bands using a Stratagene Eagle Eye II densitometer. Yield calculations assumed that species in denaturing gels stain with comparable intensity per nucleotide. The DNA-templated yields of the nine positives arising from the 37° C. Pd(II) array shown in FIG. 2b are shown in the table below.

TABLE 6

DNA-templated yields of reactions corresponding to array positives.

| substrates | | DNA-templated yields | |
|---|---|---|---|
| | | 37° C. | 25° C. |
| 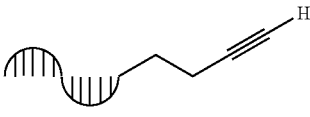 | 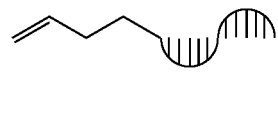 | 35 | 31 |
| 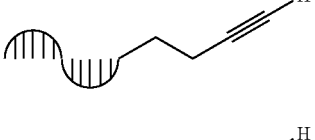 | 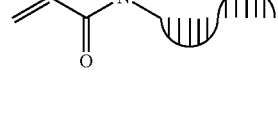 | 28 | 20 |
| 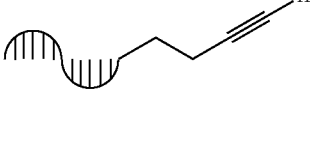 | 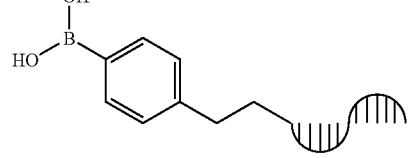 | 36 | 34 |
| 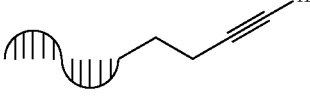 | 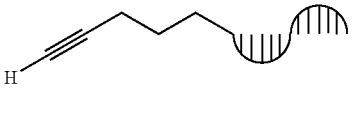 | 45 | 42 |
| 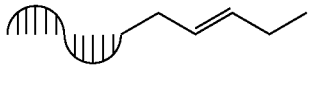 | 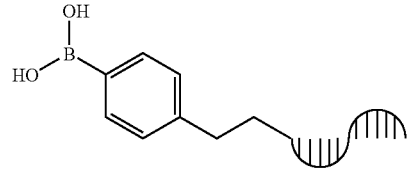 | 57 | 39 |
| 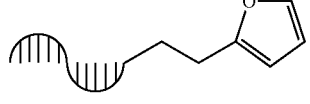 | 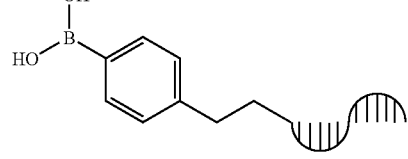 | 30 | <10 |
| 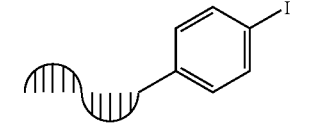 | 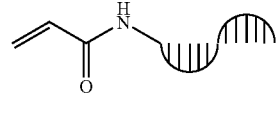 | 39 | 14 |
| 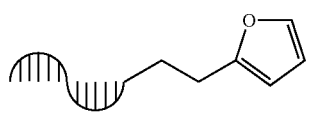 | 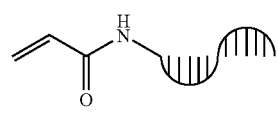 | 19 | <10 |

TABLE 6-continued

DNA-templated yields of reactions corresponding to array positives.

| substrates | DNA-templated yields | |
|---|---|---|
| | 37° C. | 25° C. |
|  | <10 | <10 |

MALDI-TOF Analysis of DNA-Templated Reaction Products

The products arising from reactions validated in a DNA-templated format by gel electrophoresis were further characterized by MALDI-TOF mass spectrometry. Two oligonucleotides were used for these experiments: a 20-base oligonucleotide labeled with a substrate at the 5' end and a 15-base oligonucleotide (complementary to a 15-base region of the 20-mer) with a 5' biotin group and a substrate attached to the 3' end through a base-labile sulfone linker. The 20-base oligonucleotide was synthesized with a 5' amine using the 5' Amino-Modifier 5 phosphoramidite and labeled using the procedures described in the preparation of substrate-linked oligonucleotides for pool A.

The 15-base oligonucleotide was synthesized with a 3' amine and a 5' biotin using the 3' Amino-Modifier C7 CPG and the 5' Biotin phosphoramidite. The oligonucleotide was labeled with a substrate via a cleavable linker in a two step procedure. In the first step, 5-10 nmol of oligonucleotide in 100 μL of 0.2 M phosphate pH 8.0 was combined with 10 μL of a 0.1 M solution of bis[2-(succinimidyloxycarbonyloxy)-ethyl]sulfone (BSOCOES, Pierce) in DMF and vortexed for 90 s. Immediately after vortexing, 9 μL of a 0.2 M solution of hexanediamine dihydrochloride salt in $H_2O$ was added and the solution was agitated at 25° C. for 1 h. The solution was then passed through a Nap-5 gel filtration column (Amersham) and the hexanediamine-labeled oligonucleotide was purified by reverse-phase HPLC. The purified oligonucleotide was then labeled with the appropriate carboxylic acid using the same procedures described above.

Substrate-linked 20-base and 15-base oligonucleotides used in these experiments were characterized by MALDI-TOF mass spectroscopy as shown in Table 7.

TABLE 7

MALDI-TOF characterization of DNA-linked substrates for characterizing reaction products in a DNA-templated format.

| Substrate | Expected mass of labeled 20-base oligonucleotide | Observed mass |
|---|---|---|
| 6-heptynoic acid | 6317.15 | 6315 ± 5 |
| 4-iodobenzoic acid | 6439.02 | 6440 ± 5 |
| 3-(2-furyl)propionic acid | 6331.13 | 6330 ± 5 |
| 4-(2-carboxyethyl) benzeneboronic acid | (citric acid adduct) 6541.2 | 6539 |

| Substrate | Expected mass of labeled 15-base oligonucleotide | Observed mass |
|---|---|---|
| acrylic acid | 5611.2 | 5610 ± 5 |
| 6-heptenoic acid | 5667.2 | 5668 ± 5 |

TABLE 7-continued

MALDI-TOF characterization of DNA-linked substrates for characterizing reaction products in a DNA-templated format.

| 4-(2-carboxyethyl) benzeneboronic acid | (citric acid adduct) 5889.2 | 5888 ± 5 |
|---|---|---|
| 6-heptynoic acid | 5665.2 | 5664 ± 5 |
| 3-hexenoic acid | 5653.2 | 5656 ± 5 |

Scheme 1: Strategy used to characterize products of DTS reactions by MALDI-TOF mass spectrometry

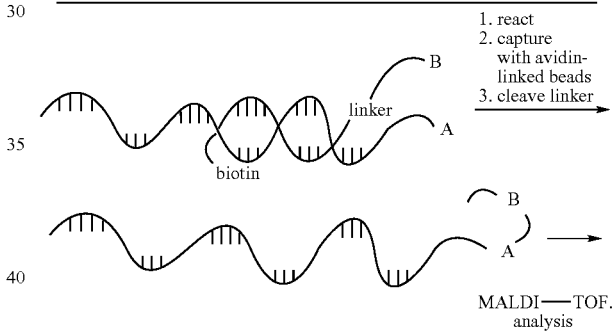

1. react
2. capture with avidin-linked beads
3. cleave linker

MALDI—TOF. analysis

To obtain a product sample suitable for MALDI-TOF analysis (Scheme 1), 50 pmol of substrate-labeled 20-mer was combined with 75 pmol of substrate-labeled 15-mer in 450 μL of 0.1 M MOPS, 1 M NaCl, pH 7.0 and allowed to hybridize for at least 20 min at 25° C. Reactions were initiated by adding 50 μL of 5 mM $Na_2PdCl_4$ in $H_2O$ and allowed to react for either 20 min at 25° C. or 1 h at 37° C. before the Pd was quenched with 5 μL 2 M β-mercaptoethanol. The DNA-linked material was precipitated with EtOH and the pellets were resuspended in 300 μL 10 mM Tris, 0.1 M NaCl, 1 mM EDTA, pH 8.2 and added to an aliquot of streptavidin magnetic particles (Roche) representing 80 pmol of biotinylated oligonucleotide binding capacity. After 15 min, the supernatant was removed and the particles were washed twice with 150 μL Milli-Q $H_2O$. The particles were then resuspended in 0.1 M CAPS, pH 11 and agitated for 15 min to effect sulfone linker cleavage. The supernatant was spin-filtered and subjected to EtOH precipitation. The pellet was resuspended in 0.1 M TEAA, desalted using a Zip-Tip cartridge (Millipore), and subjected to MALDI-TOF analysis, yielding the results in the Table 8 below.

TABLE 8

MALDI-TOF characterization of products from DNA-templated reactions.

| substrates | | possible product | expected mass | observed mass |
|---|---|---|---|---|
| alkyne-DNA | alkene-DNA | R-CH₂-CH=CH-C(O)-CH₂-CH₂-R | 6559.4 | 6557 ± 5 |
| alkyne-DNA | acrylamide-DNA | R-NH-C(O)-CH₂-CH₂-C(O)-CH₂-CH₂-R | 6505.3 | 6501 ± 5 |
| alkyne-DNA | aryl boronic acid-DNA | R-CH₂-CH₂-C₆H₄-C≡C-CH₂-CH₂-R | 6563.3 | 6563 ± 5 |
| alkyne-DNA | alkyne-DNA | R-CH₂-CH=CH-C(O)-CH₂-CH₂-R | 6559.4 | 6557 ± 5 |

TABLE 8-continued

MALDI-TOF characterization of products from DNA-templated reactions.

| substrates | | possible product | expected mass | observed mass |
|---|---|---|---|---|
| (alkene-DNA) | (4-boronic acid phenyl-DNA) | trisubstituted alkene with two R groups | 6551.3 | 6548 ± 5 |
| (furan-DNA) | (4-boronic acid phenyl-DNA) | 2,5-disubstituted furan with phenyl-R | 6577.3 | 6579 ± 5 |
| (4-iodophenyl-DNA) | (acrylamide-DNA) | cinnamamide (NHR) | 6481.3 | 6479 ± 5 |

Additional relevant reaction possibilities tested in a DNA-templated format in the presence of Pd(II) include:

Ketone (A12)+alkyne (A5): yields no product

Alkyne (A5)+azide (B9), a borderline positive by green: red fluorescence ratio quantitation: yields only very weak product formation.

Benzeneboronic acid (B8) homocoupling: yields product consistent with biphenyl formation (expected mass=6587.3; observed mass=6585±5).

Copper(I)-Mediated Degradation of DNA

To assess the effects of the Cu(I)-containing conditions used above on DNA stability, we exposed 17 pmol of a DNA 30-mer in 100 μL to 500 μM $CuSO_4$, 500 μM sodium ascorbate, 50 mM MOPS, 0.1 M $Na_2SO_4$, pH 7.0, at 25° C. for 10 min. The solution was subjected to gel filtration to remove small molecules (including Cu(I)) and then analyzed by denaturing PAGE. For comparison, identical reactions were also performed in the absence of $CuSO_4$ and sodium ascorbate. DNA staining with ethidium bromide and densitometry were used to quantitate the amount of full-length DNA remaining in each sample. The sample exposed to Cu(I) was observed to contain 52% of the full-length DNA present in the no-Cu control sample.

Synthesis and Characterization of Pent-4-enoic Acid {2-[2-(2-Pent-4-Ynoylamino-Ethoxy)-Ethoxy]-Ethyl}-Amide (1)

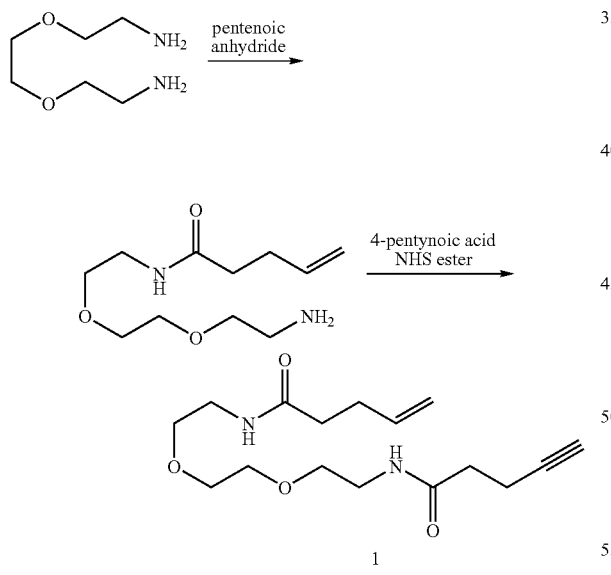

Pentenoic anhydride (789 mg, 4.3 mmol, 1.0 equiv.) in acetonitrile (10 mL) was added dropwise over the course of 30 min to a stirring solution of 2,2'-(ethylenedioxy)bis-(ethylamine) (640 mg, 4.3 mmol, 1.0 equiv.) in 20 mL acetonitrile at 25° C. At the conclusion of addition the reaction solution was dried in vacuo. The dried material was dissolved in 50 mM acetic acid in $H_2O$ (20 mL) and purified by preparative HPLC (acetonitrile/50 mM aqueous acetic acid gradient) followed by lyophilization to afford the acetate salt of the monoacylated material (560 mg, 45%) as a pale yellow oil. To the monoacylated material (300 mg, 1.0 mmol, 1.0 equiv.) in acetonitrile (20 mL) was added N-hydroxysuccinimide activated 4-pentynoic acid (220 mg, 1.1 mmol, 1.1 equiv.) and the resulting clear solution was allowed to stir under $N_2$ atmosphere at 25° C. for 20 min. The reaction was dried in vacuo, and the material was resuspended in $H_2O$ (20 mL) and purified via preparative HPLC (acetonitrile/water gradient). Lyophilization afforded 1 (230 mg, 74%, 33% overall) as an off-white crystalline solid.

$^1$H-NMR (500 MHz, $CDCl_3$): δ 6.20 (br, s, 1H, NHCO), δ 6.01 (br, s, 1H, NHCO), δ 5.86-5.78 (m, 1H, $CHCH_2$), δ 5.06 (dd, 1H, J=1.5, 17.0 Hz, $CHCH_2$), δ 4.99 (dd, 1H, J=1.5, 10.0 Hz, $CHCH_2$), δ 3.60 (s, 4H, $OCH_2CH_2O$), δ 3.55 (m, 4H, $CHOCH_2$), δ 3.47 (m, 4H, $CH_2NH$), δ 2.52 (m, 2H, $CH_2CCH$), δ 2.44-2.36 (m, 4H, $CH_2CHCH_2$, $NHCOCH_2$), δ 2.28 (t, 2H, $NHCOCH_2$), δ 2.00 (t, 1H, CCH).

$^{13}$C-NMR (100 MHz, $CDCl_3$): δ 175, 174, 137.3, 115.8, 83.2, 70.5, 70.4, 70.2, 70.1, 69.5, 39.5, 39.4, 36.0, 35.5, 29.8, 15.1.

HRMS (TOF ES$^+$) calculated for $C_{16}H_{26}N_2O_4$ $(M+H)^+$= 311.1972; observed =311.1989.

Synthesis and Characterization of 1,4-Dioxa-7,18-Diaza-Cycloicos-12-Ene-8,11,17-Trione (2)

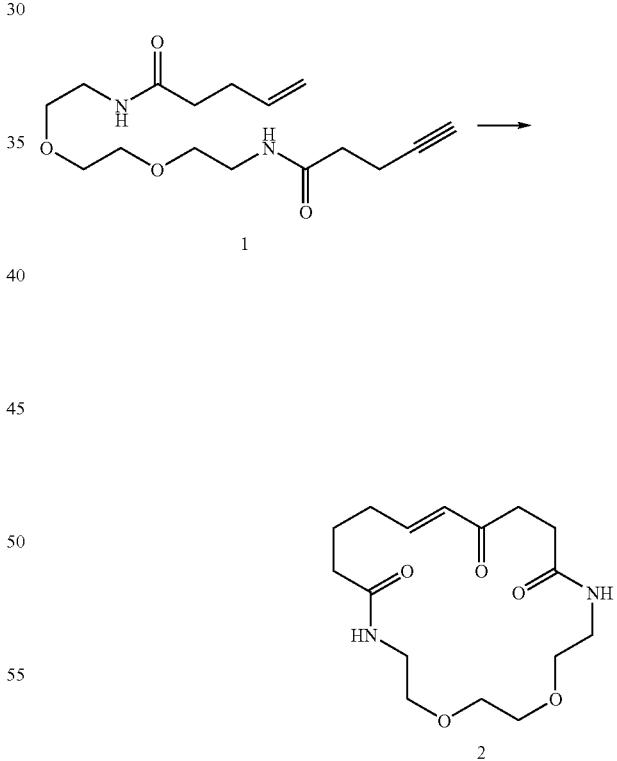

In a typical experiment, a 6 mM solution of 1 was added over the times listed in FIG. 4 to a stirring aqueous solution containing $Na_2PdCl_4$ and $CuCl_2$ in the stoichiometries listed in FIG. 4. The final concentration of 1 was typically 1.5 mM. After completion of the addition, analytical HPLC typically revealed quantitative conversion of 1 to a single product. To purify the product, the reaction was subjected to preparative reverse-phase HPLC purification with an acetonitrile/water gradient. Lyophilization of the purified material provided macrocyclic enone 2 as a yellow oil in the isolated yields reported in FIG. 4.

FIG. 4, Entry a

To a solution of $Na_2PdCl_4$ (9.4 mg, 32 µmol, 1.0 equiv.) in 1 M NaCl in water (17 mL) stirring at 25° C. open to the air was added, at a rate of 0.34 mL/h, a solution of 1 (10 mg, 32 µmol, 1.0 equiv.) in water (5.0 mL). At the completion of addition, analytical HPLC of 1.0 mL of the reaction showed quantitative conversion of starting material to a single product. To isolate the product, 20 mL of the 22 mL total reaction volume was subjected to preparative reverse-phase HPLC purification with an acetonitrile/water gradient. Lyophilization of purified material provided macrocyclic enone 2 (8.2 mg, 86%) as a yellow oil.

FIG. 4, Entry b

To a solution of $Na_2PdCl_4$ (0.49 mg, 1.6 µmol, 0.05 equiv.) in 100 mM NaCl in water (15 mL) was added $CuCl_2$ (5.4 mg, 32 µmol, 1.0 equiv.). A 6 mM solution of 1 (10 mg, 32 µmol, 1.0 equiv.) in water (5 mL) was added at 4.1 mL/h. The reaction mixture was allowed to stir at 25° C. open to the air for 1 h. Analytical HPLC of 500 µL of the reaction showed quantitative conversion of the starting material to a single product. The product was purified as described above to afford 2 (9.0 mg, 90%) as a clear oil.

FIG. 4, Entry c

To a solution of $Na_2PdCl_4$ (0.49 mg, 1.6 µmol, 0.05 equiv.) in 6.5:1 tetrahydrofuran:water (15 mL) was added $CuCl_2$ (5.4 mg, 32 µmol, 1.0 equiv.). A 6 mM solution of 1 (10 mg, 32 µmol, 1.0 equiv.) in tetrahydrofuran (5 mL) was added at 2.7 mL/h. The reaction mixture was allowed to stir at 25° C. open to the air for 2 h. Analytical HPLC of 500 µL of the reaction showed quantitative conversion of the starting material to a single product. Tetrahydrofuran was removed in vacuo, and the product was purified as described above to afford 2 (9.0 mg, 91%) as a yellow oil.

FIG. 4, Entry d

To a solution of $Na_2PdCl_4$ (1.4 mg, 4.8 µmol, 0.15 equiv.) in 9:1 tetrahydrofuran:water (40 mL) was added 1 (10 mg, 32 µmol, 1.0 equiv.). The reaction mixture was allowed to stir at 25° C. under 1 atm $O_2$ for 14 h. Following analytical HPLC of 1.0 mL of the reaction, the product was purified as described above to afford 2 (7.5 mg, 73%) as a yellow oil.

FIG. 4, Entry e

To a solution of $CuCl_2$ (2.7 mg, 16 µmol, 1.0 equiv.) in 100 mM NaCl in water (10 mL) was added 1. The reaction was allowed to stir at 25° C. open to the air for 4 h at which point 1.0 mL of the reaction mixture was subjected to analytical HPLC. No conversion of 1 to any product was observed.

FIG. 4, Entry f

To a suspension of CuCl (1.6 mg, 16 µmol, 1.0 equiv.) in 100 mM NaCl in water (10 mL) was added 1. The reaction was allowed to stir at 25° C. open to the air for 4 h at which point 1.0 mL of the reaction mixture was subjected to analytical HPLC. No conversion of 1 to any product was observed.

UV: 230 nm, 310 nm

HRMS (TOF ES$^+$) calculated for $C_{16}H_{26}N_2O_5$ (M+H)$^+$= 327.1921; found=327.1914.

$^1$H-NMR (400 MHz, CD$_3$OD): δ 6.94-6.86 (dt, 1H, J=7.2, 16 Hz, CHCHCO) δ 6.08 (dt, 1H, J=1.2, 16 Hz, CHCHCO), δ 3.62 (s, 4H. OCH$_2$CH$_2$O), δ 3.56 (t, 2H, OCH$_2$CH$_2$), δ 3.54 (t, 2H, OCH$_2$CH$_2$), δ 3.38-3.35 (m, 4H, CH$_2$NH), δ 2.92 (t, 2H, CHCOCH$_2$), δ 2.41 (t, 2H, CH$_2$CONH), δ 2.30 (m, 2H, CH$_2$CH$_2$CH), δ 2.24 (t, 2H, CH$_2$CH$_2$CONH), δ 1.91-1.82 (m, 2H, CH$_2$CH$_2$CH$_2$)—

$^1$H-NMR (500 MHz, CDCl$_3$): δ 6.83-6.77 (dt, 1H, J=7.2, 16 Hz, CHCHCO), δ 6.51 (bs, 1H, NHCO), δ 6.12-6.07 (dt, 1H, J=1.2, 16 Hz, CHCHCO), δ 6.10 (bs, 1H, NHCO), δ 3.60 (s, 4H. OCH$_2$CH$_2$O), δ 3.56 (t, 2H, OCH$_2$CH$_2$), δ 3.53 (t, 2H, OCH$_2$CH$_2$), δ 3.47-3.42 (m, 4H, CH$_2$NH), δ 2.88 (t, 2H, CHCOCH$_2$), δ 2.57 (t, 2H, CH$_2$CONH), δ 2.32 (m, 2H, CH$_2$CH$_2$CH), δ 2.18 (t, 2H, CH$_2$CH$_2$CONH), δ 1.91 (m, 2H, CH$_2$CH$_2$CH$_2$).

$^{13}$C-NMR (100 MHz, CDCl$_3$): δ 199.9, 173.0, 172.4, 148.0, 132.6, 70.8, 70.6, 70.4, 69.8, 39.5, 39.2, 35.0, 34.2, 31.6, 31.0, 23.2.

Figure 6:
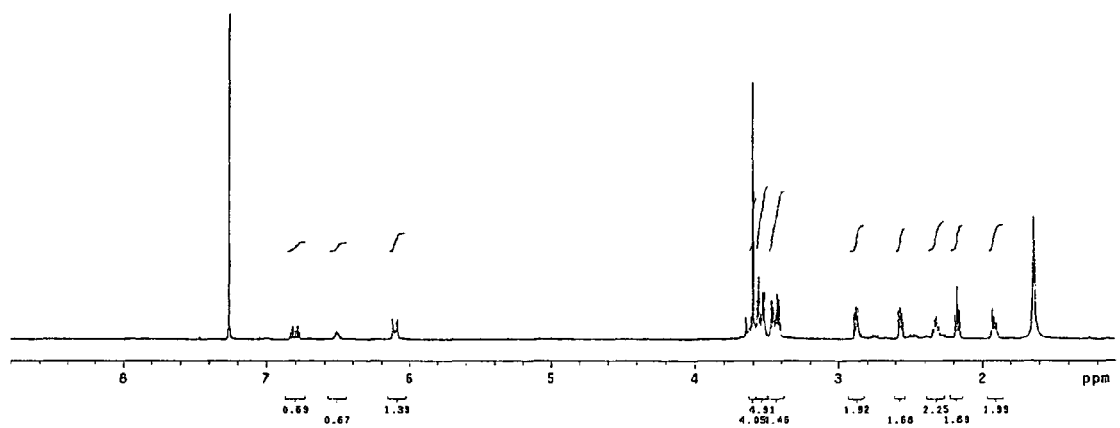
FIG. 6 shows the $^1$H NMR spectrum of a macrocyclic trans-enone product.
Figure 7:
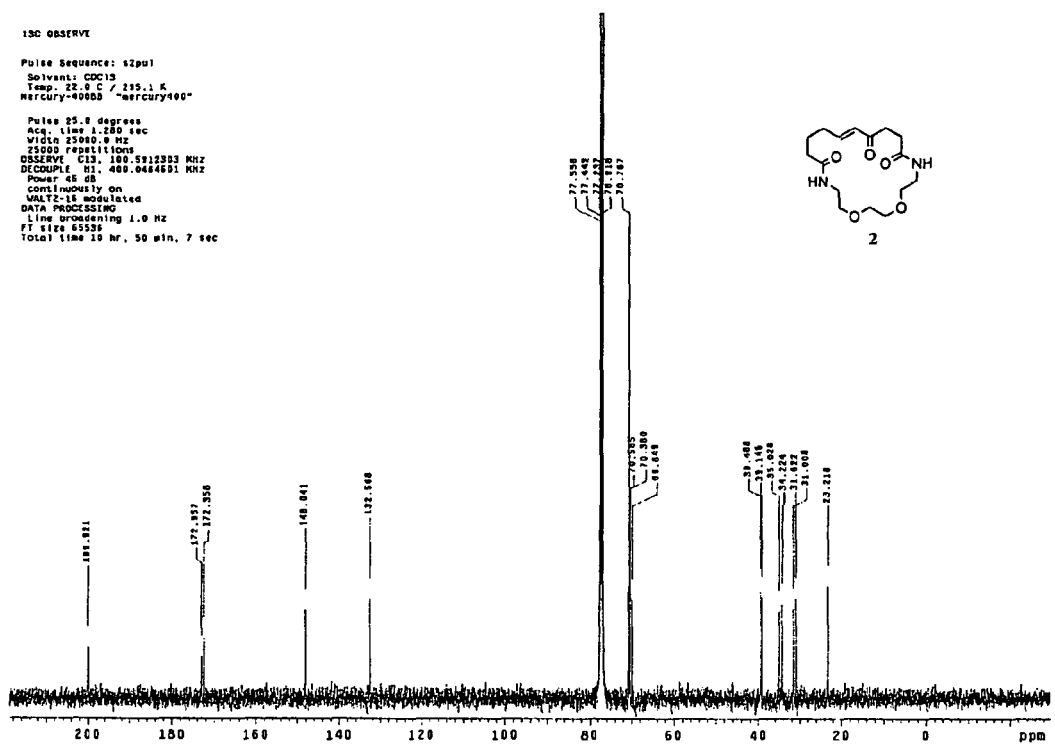
FIG. 7 shows the $^{13}$C NMR spectrum of a macrocyclic trans-enone product.
Figure 9:
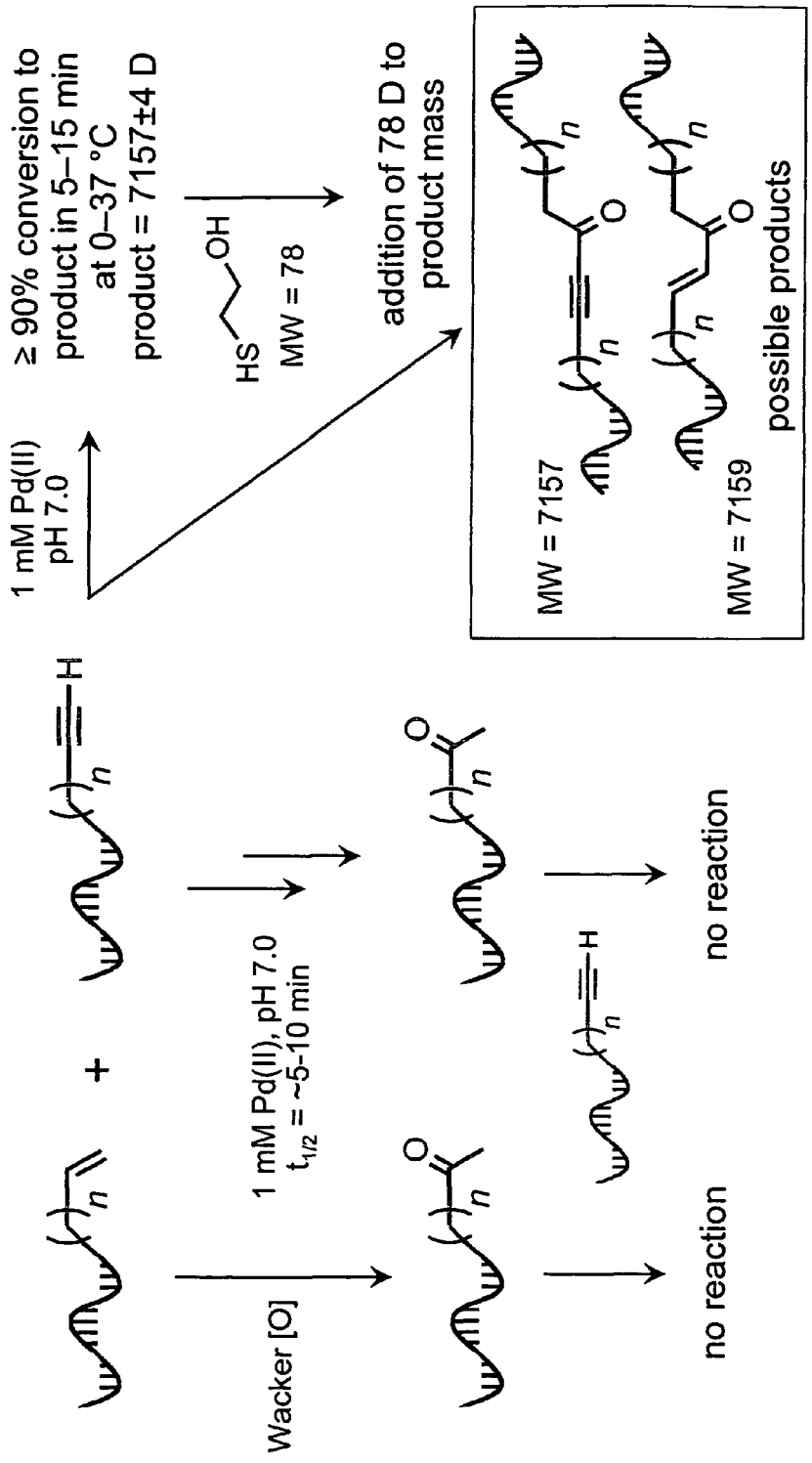
FIG. 9 shows the characterization of a new alkyne-alkene coupling reaction.
Figure 10:
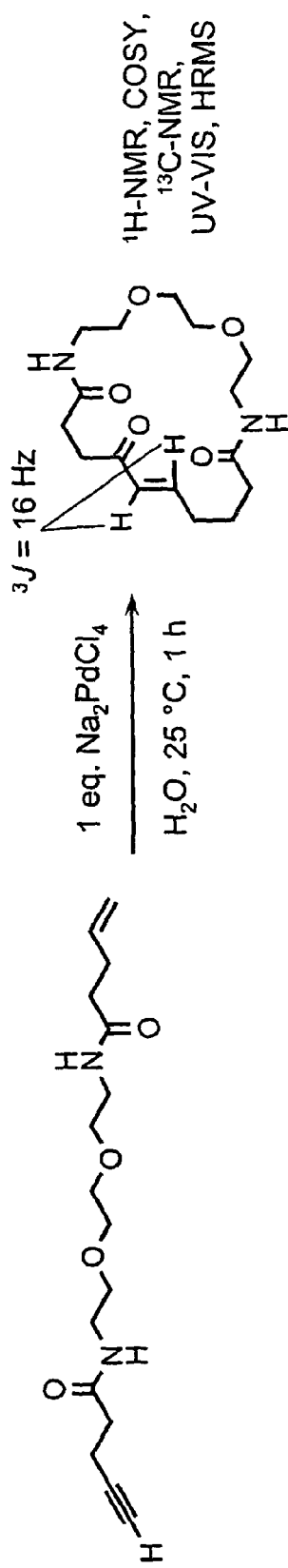
FIG. 10 shows the characterization of a macrocyclic enone resulting from the novel alkyne-alkene coupling reaction.

NMR spectra of 2 are shown in FIGS. 6-8.

Example 2
Palladium (II)-mediated oxidative coupling of terminal alkynes and terminal alkenes Both intra- and intermolecular Pd(II)-catalyzed oxidative couplings of terminal alkynes and terminal alkenes have been examined. We initially discovered that intramolecular substrate 1 forms a macrocyclic trans-disubstituted enone 2 with either stoichiometric Pd(II) or as little as 5 mol % Pd(II) and a stoichiometric oxidant such as $CuCl_2$, $O_2$, or benzoquinone. This reaction is rather insensitive to solvent composition and proceeds in aqueous NaCl, or up to 90% THF or 90% ACN. A few specific examples or reaction conditions are shown below. The reaction proceeds optimally if the substrate is slowly added to Pd(II)+oxidant. If the substrate is not added slowly, we observe significant quantities of enyne 2' by NMR. Enyne 2' may be an intermediate that undergoes a Pd(II)-mediated hydration of the alkyne to form 2 under the reaction conditions. When the substrate is not added slowly, precipitation of Pd(0) is competitive with its reoxidation to Pd(II), resulting in some portion of the macrocycles being "stuck" at the enyne stage. The enyne has not been isolated to demonstrate its conversion to enone upon exposure to additional Pd(II), although mixtures of enyne and enone do form additional enone when exposed to Pd(II).

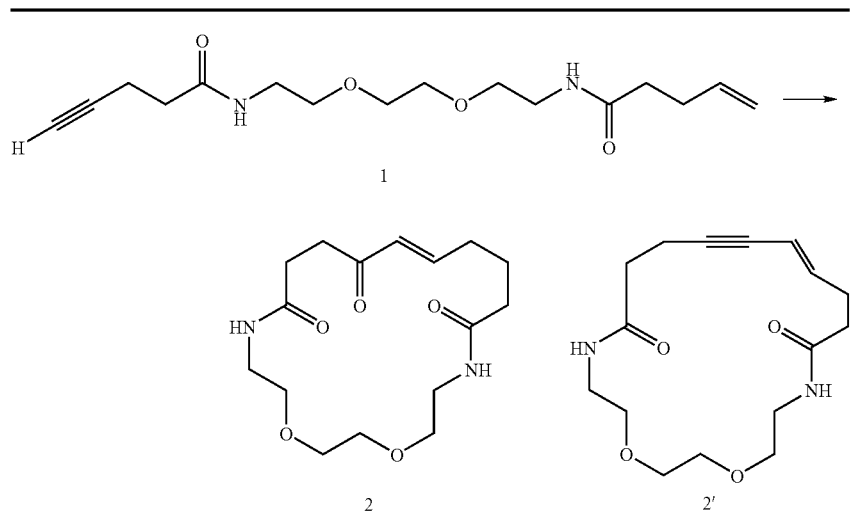
| entry | metal(s) | solvent | conditions | isolated yield of 2 |
|---|---|---|---|---|
| a | 1 equiv. Na₂PdCl₄ | 1 M NaCl in H₂O | 25° C., 15 h of 1 to Pd(II) | 86% |
| b | 5 mol % Na₂PdCl₄<br><br>1 equiv. CuCl₂ | 100 mM NaCl in H₂O | 25° C., 2 h addition of 1 to Pd(II) | 90% |
| c | 5 mol % Na₂PdCl₄<br><br>1 equiv. CuCl₂ | 9:1 THF:H₂O | 25° C, 4 h addition of 1 to Pd(II) | 91% |
| d | 15 mol % Na₂PdCl₄<br><br>1 atm O₂ | 9:1 THF:H₂O | 25° C., 14 h | 73% |

Successful macrocyclic enone formations have also been achieved with substrates related to 1. In a 60% ACN—H₂O solution with 10% PdSO₄ and benzoquinone as the terminal oxidant, substrate 3 forms macrocyclic enone 4 in 40-50% yield. Slow addition conditions for 3 are not nearly as effective as for 1. Substrate 5 undergoes cyclization to form disubstituted enone 6 and trisubstituted enone(s) 7 under conditions that are similar to those that are optimal for 3. We have used 10% Pd(II) as the upper limit for the catalyst loading for these studies. Significantly improved conversions for both 3 and 5 may be attainable with increased loadings.

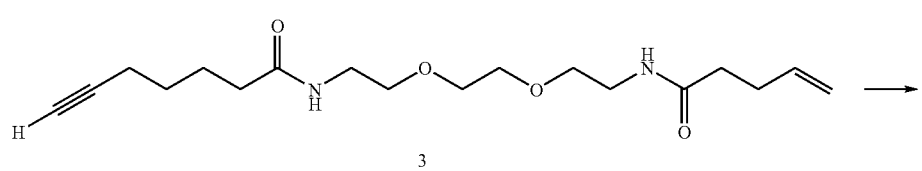

3

4

| metal(s) | solvent | conditions | HPLC yield |
|---|---|---|---|
| 10% PdSO₄ | 60% ACN | 25° C., 1 equiv. TFA or NaHSO₄, 1.5 equiv. benzoquinone 4 h, 3 mM 3 | ~40-50% |

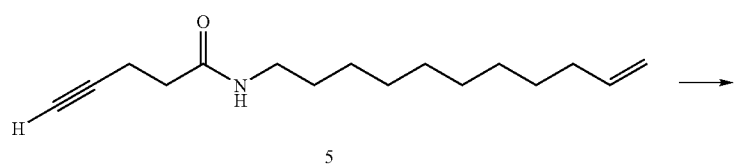

5

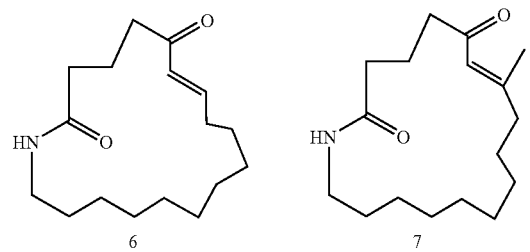

6    7

| metal(s) | solvent | conditions | HPLC yield |
|---|---|---|---|
| 10% Na₂PdCl₄ | 60% ACN | 25° C., 1.5 equiv. benzoquinone 3 h, 7 mM 5 | ~40-50% 6, <5% 7 |

We think that the amide is a ligand for Pd(II) and helps "deliver" the Pd(II) to the alkyne to initiate the reaction. This hypothesis is consistent with the relative reactivity of 1 and 3—the increased distance between the alkyne and its amide linkage in 3 results in less efficient delivery of the Pd(II) to the alkyne.

Aniline derivate 8 has been used in intermolecular reactions. These reactions use a slow addition of 8 to Pd(II)+ oxidant +olefin because 8 will react with itself under the reaction conditions if it is present in a high concentration. With the simple terminal alkene 9, trisubstituted enones are formed as minor products in addition to the disubstituted enone. These products are formed in larger amounts if the weak acid is omitted from the reaction conditions. The spacing between the amide and the alkyne is important. The addition of two more methylenes reduces the efficiency of the reaction, as seen for the reaction with substrate 15.

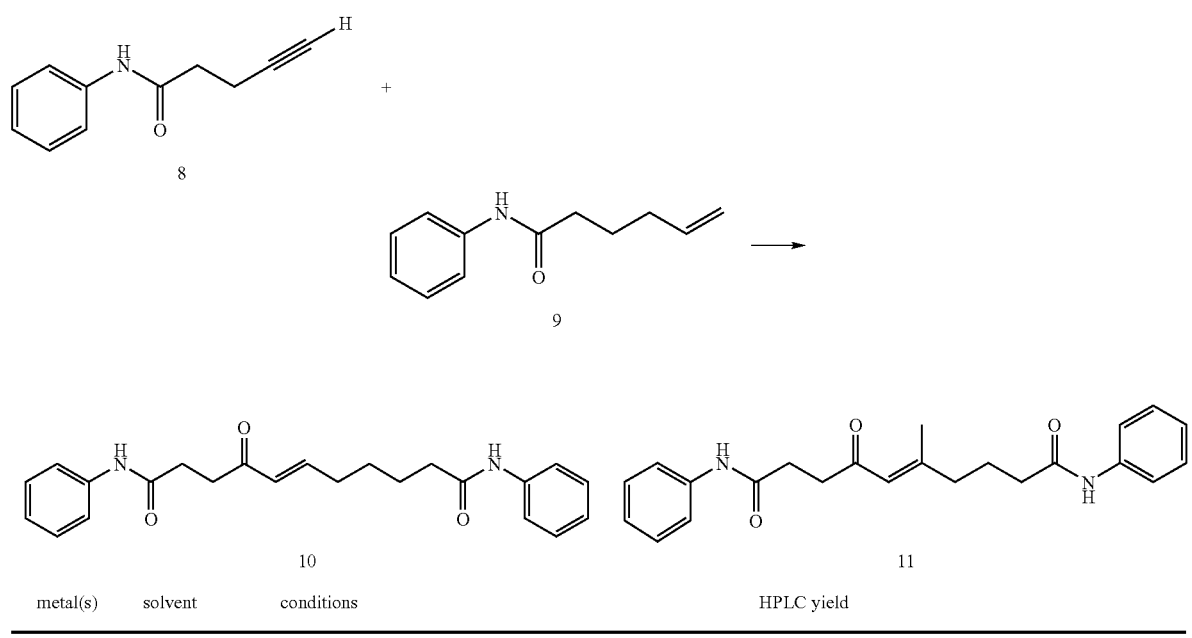

| metal(s) | solvent | conditions | HPLC yield |
|---|---|---|---|
| 10% PdCl$_2$ | 60% ACN | 25° C., 5 h addition of 8 to 1.5 equiv. 9, 1.5 equiv. benzoquinone, 1 equiv. NaHSO$_4$ | ~60-70% 10; ~10-20% 11 +12 |

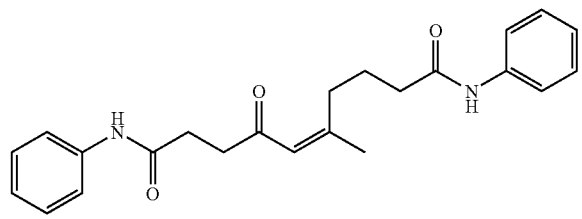

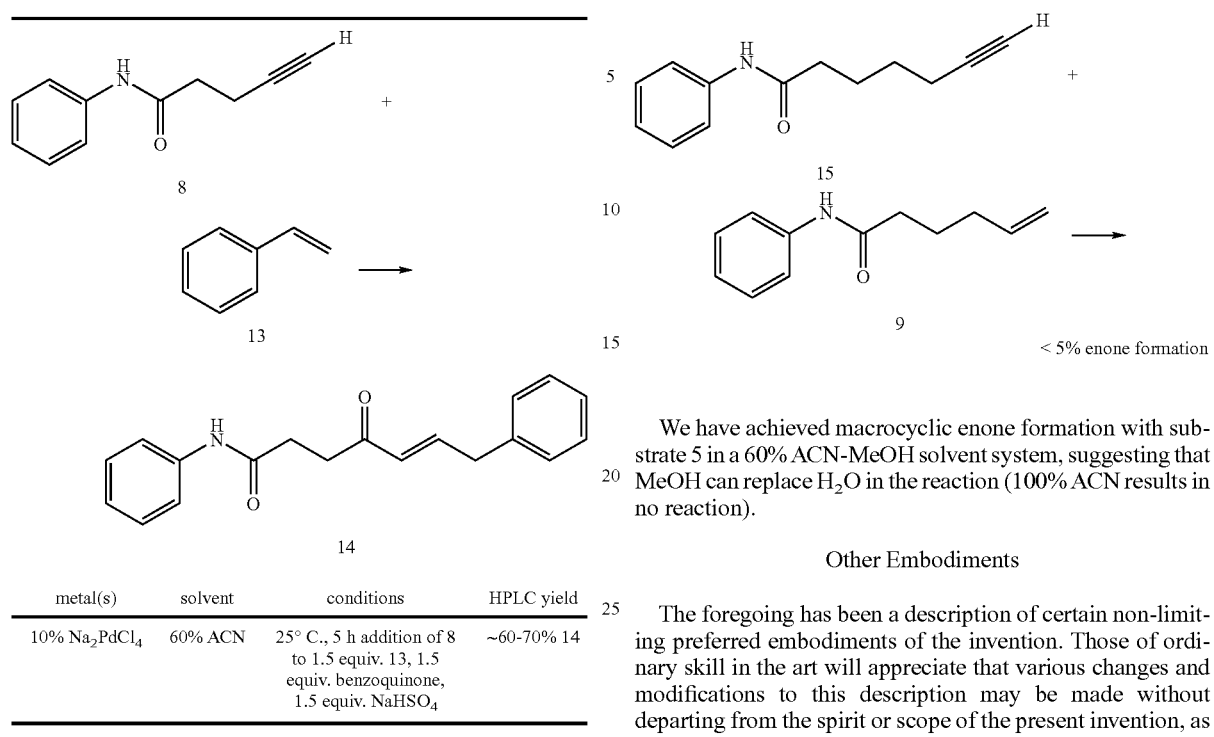

We have achieved macrocyclic enone formation with substrate 5 in a 60% ACN-MeOH solvent system, suggesting that MeOH can replace $H_2O$ in the reaction (100% ACN results in no reaction).

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of forming an enone of formula:

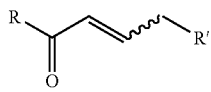

wherein R and R' are independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety, the method comprising steps of:

providing a terminal alkyne of formula:

providing an alkene of formula:

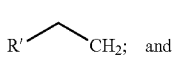

reacting the alkyne and alkene in the presence of palladium (II) under suitable conditions to form an enone.

2. The method of claim 1, wherein the enone is of the formula:

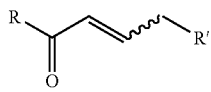

3. The method of claim 1, wherein the enone is of the formula:

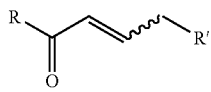

4. The method of claim 1 wherein R and R' are independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; or substituted or unsubstituted, branched or unbranched heteroaryl.

5. A method of forming an enone of formula:

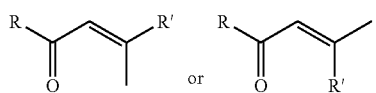

wherein R and R' are independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; =O; —$C(=O)R_A$; —$CO_2R_A$; —CN; —SCN; —$SR_A$; —$SOR_A$; —$SO_2R_A$; —$NO_2$; —$N(R_A)_2$; —$NHC(O)R_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety, the method comprising steps of:

providing a terminal alkyne of formula:

providing an alkene of formula:

reacting the alkyne and alkene in the presence of palladium (II) under suitable conditions to form an enone, wherein the oxygen of the carbonyl group of the enone is derived from water, and wherein none of the carbon or oxygen atoms in the enone are derived from carbon monoxide.

* * * * *

UNITED STATES PATENT AND TRADEMARK OFFICE
CERTIFICATE OF CORRECTION

PATENT NO.        : 7,851,658 B2
APPLICATION NO.   : 11/205493
DATED             : December 14, 2010
INVENTOR(S)       : David R. Liu et al.

It is certified that error appears in the above-identified patent and that said Letters Patent is hereby corrected as shown below:

In claim 1 at column 79, line 55, please replace the structure:

with the structure:

In claim 1 at column 79, line 65, please replace the structure:

with the structure:

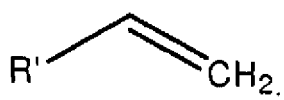

Signed and Sealed this
Twenty-second Day of March, 2011

David J. Kappos
*Director of the United States Patent and Trademark Office*

CERTIFICATE OF CORRECTION (continued)
U.S. Pat. No. 7,851,658 B2

In claim 5 at column 82, line 5, please replace the structure:

with the structure:

In claim 5 at column 82, line 15, please amend the claim as follows:
. . . reacting the alkyne and alkene in the presence of palladium (II) under suitable conditions to form an enone, ~~wherein the oxygen of the carbonyl group of the enone is derived from water, and wherein none of the carbon or oxygen atoms in the enone are derived from carbon monoxide~~.

SEQUENCE LISTING

```
<160> NUMBER OF SEQ ID NOS: 67

<210> SEQ ID NO 1
<211> LENGTH: 67
<212> TYPE: DNA
<213> ORGANISM: Artificial
<220> FEATURE:
<223> OTHER INFORMATION: Annealing Region of Pool A Oligonucleotide
      Sequence
<220> FEATURE:
<221> NAME/KEY: misc_feature
<222> LOCATION: (16)..(30)
<223> OTHER INFORMATION: n =  a, c, g, or t
<220> FEATURE:
<221> NAME/KEY: misc_feature
<222> LOCATION: (41)..(52)
<223> OTHER INFORMATION: n is a, c, g, or t

<400> SEQUENCE: 1
cgttgatatc cgcagnnnnn nnnnnnnnnn cacacaccyy nnnnnnnnnn nngccagctg      60
ctagctt                                                               67

<210> SEQ ID NO 2
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 2
aacttcctct cggga                                                      15
```

```
<210> SEQ ID NO 3
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 3
acgcgatgtt tcgac                                                    15

<210> SEQ ID NO 4
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 4
agcgttatgg tccga                                                    15

<210> SEQ ID NO 5
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 5
acatgagccc cacta                                                    15

<210> SEQ ID NO 6
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 6
ccactgttac taggg                                                    15

<210> SEQ ID NO 7
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 7
cgtgcttgag gagaa                                                    15

<210> SEQ ID NO 8
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 8
aggcctcttt agacc                                                    15
```

```
<210> SEQ ID NO 9
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 9
cttagtttcg cgcac                                                     15

<210> SEQ ID NO 10
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 10
gagggtgatg catgt                                                     15

<210> SEQ ID NO 11
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 11
gctggactag ctaca                                                     15

<210> SEQ ID NO 12
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 12
tagacacgca tgtgc                                                     15

<210> SEQ ID NO 13
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 13
tcggactttg atggc                                                     15

<210> SEQ ID NO 14
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 14
accgaagggc aatac                                                     15

<210> SEQ ID NO 15
```

```
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 15
gtcagccctt ggtat                                                         15

<210> SEQ ID NO 16
<211> LENGTH: 14
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 16
cacctaccgg tatc                                                          14

<210> SEQ ID NO 17
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 17
cagtccggta cctaa                                                         15

<210> SEQ ID NO 18
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 18
cctgagaaag aaccg                                                         15

<210> SEQ ID NO 19
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 19
ttgatgacca ggcca                                                         15

<210> SEQ ID NO 20
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 20
tgcgcaactg gtctt                                                         15

<210> SEQ ID NO 21
<211> LENGTH: 15
```

<212> TYPE: DNA
<213> ORGANISM: Artificial
<220> FEATURE:
<223> OTHER INFORMATION: Annealing Region of Pool A Oligonucleotide
      Sequence

<400> SEQUENCE: 21
tggcaaatcc agcgt                                                          15

<210> SEQ ID NO 22
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 22
gaccttggcg tttag                                                          15

<210> SEQ ID NO 23
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 23
tccaggggat gcata                                                          15

<210> SEQ ID NO 24
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 24
gcacgtacat tgctg                                                          15

<210> SEQ ID NO 25
<211> LENGTH: 15
<212> TYPE: DNA
<213> ORGANISM: Artificial
<220> FEATURE:
<223> OTHER INFORMATION: Annealing Region of Pool A Oligonucleotide
      Sequence

<400> SEQUENCE: 25
ggtgtatacg tggct                                                          15

<210> SEQ ID NO 26
<211> LENGTH: 12
<212> TYPE: DNA
<213> ORGANISM: Artificial
<220> FEATURE:
<223> OTHER INFORMATION: Coding region of Pool A Oligonucleotide
      Sequence

<400> SEQUENCE: 26
aagctgatca cg                                                             12

<210> SEQ ID NO 27
<211> LENGTH: 12
<212> TYPE: DNA

```
<213> ORGANISM: Artificial
<220> FEATURE:
<223> OTHER INFORMATION: Coding region of Pool A oligonucleotide
      sequence

<400> SEQUENCE: 27
tagtgccgtt ga                                                            12

<210> SEQ ID NO 28
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 28
accatatccc ct                                                            12

<210> SEQ ID NO 29
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 29
acgtatagcg gt                                                            12

<210> SEQ ID NO 30
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 30
agaaagtgtg cg                                                            12

<210> SEQ ID NO 31
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 31
atagttggct cc                                                            12

<210> SEQ ID NO 32
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 32
atctggaacc tc                                                            12

<210> SEQ ID NO 33
<211> LENGTH: 12
<212> TYPE: DNA
<213> ORGANISM: Artificial
```

```
<220> FEATURE:
<223> OTHER INFORMATION: Coding region of Pool A oligonucleotide
      sequence

<400> SEQUENCE: 33
attcaaccgt cg                                                        12

<210> SEQ ID NO 34
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 34
caccgaagta ac                                                        12

<210> SEQ ID NO 35
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 35
ttggagcctg at                                                        12

<210> SEQ ID NO 36
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 36
ccctccttat ca                                                        12

<210> SEQ ID NO 37
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 37
tgtcgggaca at                                                        12

<210> SEQ ID NO 38
<211> LENGTH: 12
<212> TYPE: DNA
<213> ORGANISM: Artificial
<220> FEATURE:
<223> OTHER INFORMATION: Coding region of Pool A oligonucleotide
      sequence

<400> SEQUENCE: 38
tgctaatgac gc                                                        12

<210> SEQ ID NO 39
<211> LENGTH: 60
<212> TYPE: DNA
<213> ORGANISM: Artificial
<220> FEATURE:
```

```
<223> OTHER INFORMATION: Internal Standard Oligonucleotide Sequence

<400> SEQUENCE: 39
cgttgatatc cgcaggtgca ttagcacgca cacacacctc taacacagcc gccagctgct    60

<210> SEQ ID NO 40
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 40
tcccgagagg aagttc                                                    16

<210> SEQ ID NO 41
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 41
gtcgaaacat cgcgtc                                                    16

<210> SEQ ID NO 42
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 42
tcggaccata acgctc                                                    16

<210> SEQ ID NO 43
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 43
tagtggggct catgtc                                                    16

<210> SEQ ID NO 44
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 44
ccctagtaac agtggc                                                    16

<210> SEQ ID NO 45
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 45
ttctcctcaa gcacgc                                                    16
```

<210> SEQ ID NO 46
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 46
ggtctaaaga ggcctc                                               16

<210> SEQ ID NO 47
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 47
gtgcgcgaaa ctaagc                                               16

<210> SEQ ID NO 48
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 48
acatgcatca ccctcc                                               16

<210> SEQ ID NO 49
<211> LENGTH: 15
<212> TYPE: DNA
<213> ORGANISM: Artificial
<220> FEATURE:
<223> OTHER INFORMATION: Pool B oligonucleotide sequence

<400> SEQUENCE: 49
tgtagctagt ccagc                                                15

<210> SEQ ID NO 50
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 50
gcacatgcgt gtctac                                               16

<210> SEQ ID NO 51
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 51
gccatcaaag tccgac                                               16

<210> SEQ ID NO 52
<211> LENGTH: 16
<212> TYPE: DNA
<213> ORGANISM: Artificial
<220> FEATURE:
<223> OTHER INFORMATION: Pool B oligonucleotide sequence

```
<400> SEQUENCE: 52
gtattgccct tcggtc                                                      16

<210> SEQ ID NO 53
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 53
ataccaaggg ctgacc                                                      16

<210> SEQ ID NO 54
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 54
gattaccggt aggtgc                                                      16

<210> SEQ ID NO 55
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 55
ttaggtaccg gactgc                                                      16

<210> SEQ ID NO 56
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 56
cggttctttc tcaggc                                                      16

<210> SEQ ID NO 57
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 57
tggcctggtc atcaac                                                      16

<210> SEQ ID NO 58
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 58
aagaccagtt gcgcac                                                      16

<210> SEQ ID NO 59
<211> LENGTH: 16
```

```
<212> TYPE: DNA
<213> ORGANISM: Artificial
<220> FEATURE:
<223> OTHER INFORMATION: Pool B oligonucleotide sequence

<400> SEQUENCE: 59
acgctggatt tgccac                                                16

<210> SEQ ID NO 60
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 60
ctaaacgcca aggtcc                                                16

<210> SEQ ID NO 61
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 61
tatgcatccc ctggac                                                16

<210> SEQ ID NO 62
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 62
cagcaatgta cgtgcc                                                16

<210> SEQ ID NO 63
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 63
agccacgtat acaccc                                                16

<210> SEQ ID NO 64
<211> LENGTH: 30
<212> TYPE: DNA
<213> ORGANISM: Artificial
<220> FEATURE:
<223> OTHER INFORMATION: Pool B oligonucleotide sequence

<400> SEQUENCE: 64
cgttgatatc cgcagacgcg atgtttcgac                                 30

<210> SEQ ID NO 65
<211> LENGTH: 16
<212> TYPE: DNA
<213> ORGANISM: Artificial
<220> FEATURE:
<223> OTHER INFORMATION: Pool B oligonucleotide sequence

<400> SEQUENCE: 65
```

```
gtcgaaacat cgcgtc                                                   16

<210> SEQ ID NO 66
<211> LENGTH: 20
<212> TYPE: DNA
<213> ORGANISM: Artificial
<220> FEATURE:
<223> OTHER INFORMATION: Sequence used in MALDI-TOF analysis of
      DNA-templated reactions (20-base oligonucleotides)

<400> SEQUENCE: 66
cattaccatg tacataccag                                               20

<210> SEQ ID NO 67
<211> LENGTH: 15
<212> TYPE: DNA
<213> ORGANISM: Artificial
<220> FEATURE:
<223> OTHER INFORMATION: Sequence used in MALDI-TOF analysis of
      DNA-templated reactions (15-base oligonucleotides)

<400> SEQUENCE: 67
ctggtatgta catgg                                                    15
```